United States Patent
Acosta et al.

(10) Patent No.: US 11,911,445 B2
(45) Date of Patent: *Feb. 27, 2024

(54) PEPTIDE YY PHARMACEUTICAL FORMULATIONS, COMPOSITIONS, AND METHODS

(71) Applicant: Gila Therapeutics, Inc., Minneapolis, MN (US)

(72) Inventors: Andres Acosta, Rochester, MN (US); Thomas Vasicek, Minneapolis, MN (US); Beth Anne-Szkudlarek Brown, Plymouth, MN (US)

(73) Assignee: Gila Therapeutics, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/255,105

(22) Filed: Jan. 23, 2019

(65) Prior Publication Data
US 2019/0231850 A1 Aug. 1, 2019

Related U.S. Application Data

(60) Provisional application No. 62/669,191, filed on May 9, 2018, provisional application No. 62/620,580, filed on Jan. 23, 2018.

(51) Int. Cl.

| | |
|---|---|
| *A61K 38/22* | (2006.01) |
| *A61K 9/00* | (2006.01) |
| *A61P 3/04* | (2006.01) |
| *A61K 47/38* | (2006.01) |
| *A61K 9/48* | (2006.01) |
| *A61K 9/20* | (2006.01) |
| *A61K 47/02* | (2006.01) |
| *A61K 9/16* | (2006.01) |
| *A61K 47/26* | (2006.01) |
| *A61K 47/10* | (2017.01) |
| *A61K 47/12* | (2006.01) |
| *A61K 47/46* | (2006.01) |
| *A61K 9/68* | (2006.01) |
| *A61K 47/32* | (2006.01) |
| *A61K 9/19* | (2006.01) |
| *A61K 47/18* | (2017.01) |

(52) U.S. Cl.
CPC ............. *A61K 38/22* (2013.01); *A61K 9/006* (2013.01); *A61K 9/0056* (2013.01); *A61K 9/0058* (2013.01); *A61K 9/0063* (2013.01); *A61K 9/0075* (2013.01); *A61K 9/1623* (2013.01); *A61K 9/19* (2013.01); *A61K 9/205* (2013.01); *A61K 9/2013* (2013.01); *A61K 9/2018* (2013.01); *A61K 9/2027* (2013.01); *A61K 9/2054* (2013.01); *A61K 9/4858* (2013.01); *A61K 9/4866* (2013.01); *A61K 47/02* (2013.01); *A61K 47/10* (2013.01); *A61K 47/12* (2013.01); *A61K 47/183* (2013.01); *A61K 47/26* (2013.01); *A61K 47/32* (2013.01); *A61K 47/38* (2013.01); *A61K 47/46* (2013.01); *A61P 3/04* (2018.01)

(58) Field of Classification Search
CPC .... A61K 38/22; A61K 9/0056; A61K 9/0058; A61K 9/006
See application file for complete search history.

(56) References Cited

U.S. PATENT DOCUMENTS

| | | |
|---|---|---|
| 6,558,708 B1 | 5/2003 | Lin |
| 7,157,426 B2 | 1/2007 | Quay et al. |
| 7,166,575 B2 | 1/2007 | Quay |
| 7,186,691 B2 | 3/2007 | Quay et al. |
| 7,186,692 B2 | 3/2007 | Quay et al. |
| 7,208,186 B2 | 4/2007 | Norman et al. |
| 7,244,412 B2 | 7/2007 | Lin |
| 7,459,432 B2 | 12/2008 | Cowley et al. |
| 7,608,245 B2 | 10/2009 | Lin |
| 7,615,207 B2 | 11/2009 | Lin |
| 7,745,216 B2 | 6/2010 | Pang et al. |
| 8,202,836 B2 | 6/2012 | Moore et al. |
| 8,217,001 B2 | 7/2012 | Cowley et al. |
| 8,273,713 B2 | 9/2012 | Pittner et al. |
| 8,273,794 B2 | 9/2012 | Gomez-Orellana et al. |
| 8,283,312 B2 | 10/2012 | Meguid et al. |
| 8,486,646 B2 | 7/2013 | Chu et al. |

(Continued)

FOREIGN PATENT DOCUMENTS

| | | |
|---|---|---|
| CN | 107778336 A | 3/2018 |
| EP | 2155229 B1 | 1/2011 |

(Continued)

OTHER PUBLICATIONS

Pai, Drug Dosing Based on Weight and Body Surface Area: Mathematical Assumptions and Limitations in Obese Adults, Pharmacotherapy 2012;32(9):856-868) (Year: 2012).*
Nayak et al., "Current developments in orally disintegrating tablet technology," J Pharm Educ Res 2:21-34 (2011) (Year: 2011).*
Patel et al., "A Review: Formulation of Fast Dissolving Tablet," PharmaTutor Magazine 2:30-45 (2014) (Year: 2014).*
"Vetter—Packaging systems and technologies for pharmaceutical products," Vetter, Date Accessed; Apr. 10, 2019, https://www.vetter-pharma.com/en/clinical-manufacturing/packaging/systems.
Acosta et al., "Challenges and Opportunities in Management of Obesity," Gut, Apr. 2014, vol. 63(4), pp. 687-695.
Aslani et al., "Medicated chewing gum, a novel drug delivery system," J. Res Med Sci., Apr. 2015, vol. 20(4), pp. 403-411.

(Continued)

Primary Examiner — Julie Ha
Assistant Examiner — Kristina M Hellman
(74) Attorney, Agent, or Firm — Clark & Elbing LLP

(57) ABSTRACT

Pharmaceutical compositions comprising PYY (e.g., PYY (3-36) and analogs and variants thereof), satiety peptides, satiety hormones, metabolic hormones, and methods of treating metabolic diseases with such compositions are provided. Aspects include methods of increasing a feeling of fullness in patients treated with pharmaceutical compositions comprising PYY, PYY(3-36), satiety peptides, satiety hormones, metabolic hormones, and analogs, receptor antagonists and variants thereof.

13 Claims, 3 Drawing Sheets

Specification includes a Sequence Listing.

(56) References Cited

U.S. PATENT DOCUMENTS

| | | | |
|---|---|---|---|
| 9,018,160 | B2 | 4/2015 | Bloom |
| 9,149,478 | B2 | 10/2015 | Klein et al. |
| 9,186,392 | B2 | 11/2015 | Klein et al. |
| 9,211,263 | B2 | 12/2015 | Baron et al. |
| 9,399,054 | B2 | 7/2016 | Dinh et al. |
| 9,457,029 | B2 | 10/2016 | Dugi et al. |
| 9,492,505 | B2 | 11/2016 | Zolotukhin et al. |
| 9,693,968 | B2 | 7/2017 | Schentag et al. |
| 11,103,556 | B2 | 8/2021 | Zolotukhin et al. |
| 11,311,633 | B2 | 4/2022 | Zolotukhin et al. |
| 2005/0002927 | A1 | 1/2005 | Quay et al. |
| 2006/0046962 | A1 | 3/2006 | Meezan et al. |
| 2007/0104763 | A1 | 5/2007 | Jobdevairakkam et al. |
| 2007/0149451 | A1 | 6/2007 | Holmes |
| 2007/0213270 | A1* | 9/2007 | Costantino ............ A61K 31/724 514/5.2 |
| 2007/0275893 | A1 | 11/2007 | Quay |
| 2008/0125360 | A1 | 5/2008 | Nilsson |
| 2008/0255250 | A1 | 10/2008 | Gomez-Orellana et al. |
| 2009/0209461 | A1 | 8/2009 | Cowley et al. |
| 2010/0055179 | A1* | 3/2010 | Park ..................... A61K 9/0056 424/465 |
| 2010/0092564 | A1* | 4/2010 | Park ..................... A61K 9/2018 424/489 |
| 2010/0111902 | A1 | 5/2010 | Durfee et al. |
| 2011/0183898 | A1 | 7/2011 | Dinh |
| 2012/0003316 | A1* | 1/2012 | Reddy ................. A61K 31/135 424/487 |
| 2012/0035100 | A1 | 2/2012 | Zolotukhin et al. |
| 2012/0094903 | A1 | 4/2012 | Constantino et al. |
| 2013/0324463 | A1 | 12/2013 | Klein et al. |
| 2014/0287001 | A1 | 9/2014 | Shailubhai |
| 2014/0357552 | A1 | 12/2014 | Asami et al. |
| 2015/0031630 | A1 | 1/2015 | Nestor |
| 2015/0105318 | A1 | 4/2015 | Graefe-Mody et al. |
| 2015/0250856 | A1* | 9/2015 | Schwarz ............. A61K 9/2018 514/5.9 |
| 2017/0080056 | A1 | 3/2017 | Zolotukhin et al. |
| 2017/0137486 | A1 | 5/2017 | Bloom |
| 2017/0304404 | A1 | 10/2017 | Costello et al. |
| 2017/0326257 | A1 | 11/2017 | Zolotukhin et al. |
| 2018/0051012 | A1 | 2/2018 | Boehm et al. |
| 2019/0224280 | A1 | 7/2019 | Acosta et al. |
| 2020/0061158 | A1 | 2/2020 | Zolotukhin et al. |
| 2021/0308223 | A1 | 10/2021 | Acosta et al. |
| 2021/0401942 | A1 | 12/2021 | Zolotukhin et al. |
| 2022/0143146 | A1 | 5/2022 | Acosta et al. |
| 2022/0280658 | A1 | 9/2022 | Zolotukhin et al. |

FOREIGN PATENT DOCUMENTS

| | | | |
|---|---|---|---|
| EP | 2387993 | A1 | 11/2011 |
| JP | 2005-508324 | A | 3/2005 |
| JP | 2006-516262 | A | 6/2006 |
| JP | 2008514616 | A | 5/2008 |
| JP | 2009500453 | A | 1/2009 |
| MX | PA02010030 | A | 9/2003 |
| WO | WO-2003/026591 | A2 | 4/2003 |
| WO | 2003057235 | A2 | 7/2003 |
| WO | WO-2003/057170 | A2 | 7/2003 |
| WO | WO-2005/080433 | A2 | 9/2005 |
| WO | WO-2005/110467 | A1 | 11/2005 |
| WO | WO-2006/017251 | A2 | 2/2006 |
| WO | WO-2008/109068 | A2 | 9/2008 |
| WO | WO-2010/090876 | A2 | 8/2010 |
| WO | WO-2017/009236 | A1 | 1/2017 |
| WO | 2017191274 | A2 | 11/2017 |
| WO | 2017204219 | A1 | 11/2017 |
| WO | WO-2019/139934 | A1 | 7/2019 |
| WO | WO-2019/147650 | A1 | 8/2019 |
| ZA | 200508848 | B | 9/2006 |

OTHER PUBLICATIONS

Aungst et al., "Comparison of the effects of various transmucosal absorption promoters on buccal insulin delivery," International Journal of Pharmaceutics, Aug. 1, 1989, vol. 53(3), pp. 227-235.

Bala et al., "Orally dissolving strips: A new approach to oral drug delivery system," Int J Pharm Investig, Apr.-Jun. 2013, vol. 3(2), pp. 67-76.

Batterham et al., "Gut hormone PYY3-36 physiologically inhibits food intake," Nature, Aug. 8, 2002, vol. 418, pp. 650-654.

Blundell et al., "Appetite control: methodological aspects of the evaluation of foods," Obes Rev, Mar. 2010, vol. 11(3), pp. 251-270.

Bray et al., "Update on obesity pharmacotherapy," Annals of the New York Academy of Sciences 1311, 2014, pp. 1-13.

Chaudhari et al., "Formulation and Evaluation of Buccal Tablet of Salbutamol Sulphate," IRJP, 2011, vol. 2(12), pp. 238-242.

Cutter et al., "Development of a multiple sclerosis functional composite as a clinical trial outcome measure," Brain, May 1999, vol. 122(5), pp. 871-882.

Delgado-Aros et al., "Effect of GLP-1 on gastric volume, emptying, maximum volume ingested, and postprandial symptoms in humans," American journal of physiology, Gastrointestinal and liver physiology, Mar. 2002, vol. 282(3), G424-G431.

Elnaggar et al., "Maltodextrin: A Novel Excipient Used in Sugar-Based Orally Disintegrating Tablets and Phase Transition Process," AAPS PharmSciTech, Jun. 2010, vol. 11(2), pp. 645-651.

Flegal et al., "Prevalence of Obesity and Trends in the Distribution of Body Mass Index Among US Adults, 1999-2010," JAMA, Feb. 1, 2012, vol. 307(5), pp. 491-497.

Flint et al., "Reproducibility, power and validity of visual analogue scales in assessment of appetite sensations in single test meal studies," International Journal of Obesity, Feb. 4, 2000, vol. 24, pp. 38-48.

Gardiner et al., "Gut Hormones: A Weight Off Your Mind," J Neuroendocrinol, Jun. 2008, vol. 20(6), pp. 834-841.

Heema et al., "Medicated chewing gums—updated review," Int J Pharm Res Dev, 2010, vol. 2(8), pp. 66-76.

Huang et al., "Using spray-dried lactose monohydrate in wet granulation method for a low-dose oral formulation of a paliperidone derivative," Powder Technology, Sep. 2013, vol. 246, pp. 379-394.

International Search Report and Written Opinion dated Jun. 14, 2019 for International Patent Application No. PCT/US2019/014720.

Invitation to Pay Additional Fees and, Where Applicable, Protest Fee dated Apr. 17, 2019 for International Patent Application No. PCT/US2019/014720.

Jayasena et al., "Role of Gut Hormones in Obesity," Endocrinology and Metabolism Clinics of North America, Sep. 2008, vol. 37(3), pp. 769-787.

Kamini et al., "Formulation and Percentage Evaluation of Gum-Acacia as a Binder W.S.R. to Jwaraghani Gutika (Herbo-Mineral Preparation)," Int J Res Med, 2016, vol. 5(1), pp. 21-24.

Koda et al., "The role of the vagal nerve in peripheral PYY3-36-induced feeding reduction in rats," Endocrinology, May 1, 2005, Vo. 146(5), pp. 2369-2375.

La Sala et al., "Modulation of taste responsiveness by the satiation hormone peptide YY," The FASEB Journal, Dec. 2013, vol. 27(12), pp. 5022-5033.

Le Roux et al. "Attenuated peptide YY release in obese subjects is associated with reduced satiety," Endocrinology, Jan. 1, 2006, vol. 147(1), pp. 3-8.

Lenard et al., "Central and Peripheral Regulation of Food Intake and Physical Activity: Pathways and Genes," Obesity, Dec. 2008, vol. 16(S3), pp. S11-S22.

Linnebjerg et al., "Effect of exenatide on gastric emptying and relationship to postprandial glycemia in type 2 diabetes," Regulatory Peptides, Nov. 29, 2008, vol. 151(1-3), pp. 123-129.

Luhn, "Using Excipients in Powder Formulations," Pharmaceutical Technology Europe, Jan. 7, 2011, vol. 23(1).

Michel et al., "Dipeptidyl peptidase IV inhibitors in diabetes; more than inhibition of glucagon-like peptide-1 metabolism?," Naunyn-Schmiedeberg's Arch Pharmacol, May 2008, vol. 377(3), pp. 205-207.

(56) References Cited

OTHER PUBLICATIONS

Moreno et al., "Exenatide as a Novel Weight Loss Modality in Patients Without Diabetes," Annals of Pharmacotherapy, Dec. 2012, vol. 46(12), pp. 1700-1706.

Ng et al., "Global, regional and national prevalence of overweight and obesity in children and adults 1980-2013: A systematic analysis," Lancet, Aug. 30, 2014, vol. 384(9945), pp. 766-781.

Niida et al., "Antiobesity and emetic effects of a short-length peptide YY analog and its PEGylated and alkylated derivatives," Bioorganic & Medicinal Chemistry, Feb. 1, 2018, vol. 26(3), pp. 566-572.

Ogden et al., "The Epidemiology of Obesity," Gastroenterology, May 2007, vol. 132(6), pp. 2087-2102.

Peters, "Incretin-Based Therapies: Review of Current Clinical Trial Data," The American Journal of Medicine, Mar. 2010, vol. 123(3), pp. S28-S37.

Shirsand et al., "Formulation and optimization of mucoadhesive bilayer buccal tablets of atenolol using simplex design method," Int J Pharm Investig, Jan.-Mar. 2012, vol. 2(1), pp. 34-41.

Tomar et al., "Formulation and Evaluation of Fast Dissolving Oral Film of Dicyclomine as potential route of Buccal Delivery," Intl Journl of Drug Development & Research, Apr.-Jun. 2012, vol. 4(2), pp. 408-417.

Van Can et al., "Effects of the once-daily GLP-1 analog liraglutide on gastric emptying, glycemic parameters, appetite and energy metabolism in obese, non-diabetic adults," International Journal of Obesity, 2014, vol. 38, pp. 784-793.

Verdich et al., "A Meta-Analysis of the Effect of Glucagon-Like Peptide-1 (7-36) Amide on Ad Libitum Energy Intake in Humans," The Journal of Clinical Endocrinology & Metabolism, Sep. 1, 2001, vol. 86(9), pp. 4382-4389.

White et al., "Alogliptin after Acute Coronary Syndrome in Patients with Type 2 Diabetes," N Engl J Med, Oct. 3, 2013, vol. 369(14), pp. 1327-1335.

Wieland et al., "Receptor binding profiles of NPY analogues and fragments in different tissues and cell lines," Peptides, 1995, vol. 16(8), pp. 1389-1394.

Wu et al., "Studies on the spray dried lactose as carrier for dry powder inhalation," Asian Journal of Pharmaceutical Sciences, Dec. 2014, vol. 9(6), pp. 336-341.

International Preliminary Report on Patentability dated Aug. 6, 2020, issued in International Application No. PCT/US2019/014720.

Hurtado et al., "Distribution of Y-Receptors in Murine Lingual Epithelia," PLoS One. 7(9):e46358 (2012) (12 pages).

Tsumoto et al., "Role of arginine in protein refolding, solubilization, and purification," Biotechnol Prog. 20(5):1301-8 (2004).

Rondanelli et al., "Satiety and amino-acid profile in overweight women after a new treatment using a natural plant extract sublingual spray formulation," Int J Obes (Lond). 33(10):1174-82 (2009).

Hurtado et al., "Salivary peptide tyrosine-tyrosine 3-36 modulates ingestive behavior without inducing taste aversion," J Neurosci. 33(47):18368-80 (2013).

Acosta et al., "Salivary PYY: a putative bypass to satiety," PLoS One. 6(10):e26137 (2011) (10 pages).

Bhati et al., "A Detailed Review on Oral Mucosal Drug Delivery System," International Journal of Pharmaceutical Sciences and Research. 3(1):659-81 (2012).

Anderson et al., Chapter 11: Excipients for Oral Liquid Formulations. *Excipient Development for Pharmaceutical, Biotechnology, and Drug Delivery Systems*. CRC Press, 155-80 (2006).

Extended European Search Report for European Patent Application No. 19744391.4, dated Sep. 22, 2021 (11 pages).

U.S. Appl. No. 17/730,960, Acosta et al.

Gutniak et al., "Potential therapeutic levels of glucagon-like peptide I achieved in humans by a buccal tablet," Diabetes Care. 19(8):843-8 (Aug. 1996).

Iepsen et al., "Therapies for inter-relating diabetes and obesity—GLP-1 and obesity," Expert Opin Pharmacother. 15(17):2487-500 (Dec. 2014).

Verma et al., "Emerging Trends in Noninvasive Insulin Delivery," J Pharm (Cairo). 2014:378048 (May 2014) (10 pages).

International Search Report and Written Opinion for PCT/US2022/036439, dated Mar. 22, 2023 (15 pages).

Batterham et al., "Inhibition of food intake in obese subjects by peptide YY3-36," N Engl J MEd. 349(10):941-8 (Sep. 2003).

* cited by examiner

PEPTIDE YY PHARMACEUTICAL FORMULATIONS, COMPOSITIONS, AND METHODS

CROSS-REFERENCE TO RELATED APPLICATIONS

This application claims priority to and the benefit of U.S. Provisional Application No. 62/620,580 filed Jan. 23, 2018 and U.S. Provisional Application No. 62/669,191 filed May 9, 2018, which are hereby incorporated by reference in their entirety.

SEQUENCE LISTING

The instant application contains a Sequence Listing which has been filed electronically in ASCII format and is hereby incorporated by reference in its entirety. Said ASCII copy, created on Feb. 27, 2019, is named 1976-0011US01_SL.txt and is 2,169 bytes in size.

All references cited herein, including but not limited to patents and patent applications, are incorporated by reference in their entirety.

BACKGROUND

The prevalence of obesity continues to increase worldwide [1]. In the United States, 69% of adults are overweight or obese [2]. However, there is still a lack of effective, long-term, noninvasive treatments for obesity. The current "one treatment fits all" approach to obesity is associated with highly variable efficacy and outcomes [3].

PYY(3-36) is a Y receptor (e.g., Y2 receptor) agonist released from intestinal cells in response to feeding. Peptide YY (PYY) (3-36) is a satiation gut hormone released postprandially, mainly by the gut. PYY(3-36) secretion is related to caloric intake, and it induces satiation by acting on Y2 receptors in the arcuate nucleus of the hypothalamus. Recently, murine and human PYY(3-36) was found to be present in saliva, and its concentration in saliva is correlated to its concentration in plasma. PYY(3-36) and Y2 receptors are expressed in the taste cells in the circumvallate papilla of the tongue [4]. In mice, acute augmentation therapy with salivary PYY(3-36) induces higher satiation shown by feeding behavioral studies, and by c-Fos activation in the arcuate nucleus of the hypothalamus. Acute increase of salivary PYY(3-36) resulted in a decrease in one-hour food intake in a dose dependent manner. The chronic over-expression of salivary PYY(3-36) using a viral vector-mediated gene delivered (rAAV-PYY vs rAAV-GFP control) into submandibular salivary glands produced a two-fold chronic increase of PYY(3-36) in saliva for 22 weeks [4]. The results of this treatment showed a decrease in weekly food intake, and a 23% body weight loss 8 weeks after vector delivery compared to a control. PYY(3-36) induces satiation through saliva and taste cell receptors [5,6].

Incretins, such as glucagon-like peptide 1 (GLP-1), enhance glycemic control, impede gastric emptying, and increase satiation in healthy and in diabetic patients [7-9]. GLP-1 and GLP-1 agonists reduce fasting and postprandial glucose levels via increased insulin secretion from the pancreas, and reduced gluconeogenesis in the liver.

Exenatide (Exendin-4) is a 39-amino acid peptide produced in the salivary gland of the Gila monster lizard. Its amino acid sequence shares 53% identity with GLP-1, but its half-life is prolonged due to its resistance to rapid breakdown by dipeptidyl peptidase 4 (DPP-IV), the normal mechanism for GLP-1 inactivation. Exenatide, in both daily and weekly formulations, has been approved by the FDA for treatment of patients with type 2 diabetes mellitus, where treatment with metformin or sulfonylureas inadequately controls the patient's condition. GLP-1 receptor agonists also retard gastric emptying and decrease food intake by 19% [10-12]. The effects of exenatide on gastric emptying are temporally associated with reduced postprandial glycemia in patients with type 2 diabetes mellitus [13].

Previously, PYY and PYY analogs were administered to patients in a manner resulting in a substantial increase in PYY levels in the plasma of the subject. PYY and PYY analogs have also been used to induce satiation in a subject without substantially changing the concentration of PYY in the plasma of the subject. See, e.g., U.S. Pat. No. 9,492,505. Higher doses of PYY may result in undesirable side effects such as nausea. However, suitable low-dose PYY pharmaceutical formulations for inducing a feeling of fullness in a subject have not been described.

SUMMARY

It has been shown that local oral delivery of PYY(3-36) reduces food intake and increases satiety. However, it is desirable to improve the activity of PYY(3-36), PYY analogs, and satiety peptides by providing a suitable low-dose formulation to induce a long lasting feeling of fullness in a subject. In addition, such formulations can be used for treatment of metabolic disorders.

Aspects described herein provide pharmaceutical compositions comprising PYY or PYY analogs (e.g., PYY(3-36)), variants, and satiety peptides (e.g., GLP-1, oxyntomodulin, and cholecystokinin) wherein the dose of PYY or PYY analogs, variants, and satiety peptides in the pharmaceutical composition is at least about 2.5 ng. In another aspect, PYY is PYY(3-36). In yet another aspect, the dose of PYY in the pharmaceutical composition is from about 2.5 ng to about 2.5 mg. In another aspect, the dose of PYY in the pharmaceutical formulation is from about 2.5 µg to about 250 µg. The term "dose" refers to an amount in the range of 90 to 110% of the desired amount of an active pharmaceutical ingredient in a dosage form or the claimed amount on a label for a Federal Drug Administration (FDA) approved drug product.

In another aspect, the dose per volume of PYY(3-36) can range, for example, from about 2.5 ng to about 250 µg in a volume from about 25 µl to about 100 µl or up to about 5 mls. In another aspect, the dose/volume is about 2.5 µg/ml. In another aspect, the dose/volume is about 500 µg/500 µL. In another aspect, the dose/volume is about 250 µg/ml.

In these aspects, the pharmaceutical compositions can further comprise pharmaceutically acceptable excipients (e.g., propylene glycol, potassium sorbate, 1-arginine, edetate disodium, monosodium phosphate, and polysorbate 20). Optionally, the pharmaceutical formulations further comprise water or any other suitable diluent or pharmaceutically acceptable excipient. In one aspect, the pharmaceutical composition comprises excipients that further stabilize PYY (3-36) at a low dose per volume (e.g., less than 2.5 ng/ml). In other aspects, the excipients increase residence time of the pharmaceutical compositions on the tongue, for example, promoting binding of PYY(3-36) to its receptor (e.g., Y2 receptor). In yet another aspect, excipients can be used to increase retention time of PYY(3-36) in the saliva, to the extent such an increase is desirable.

In another aspect, the pH of the pharmaceutical compositions is maintained at a pH which promotes the activity and stability of PYY(3-36). In one aspect, the pH of the pharmaceutical composition is between about pH 5 to about 8. In another aspect, the pH of the pharmaceutical composition is between about pH 6 to about 7. In yet another aspect, the pH is about 5.

In one aspect, the described pharmaceutical formulations can be used to treat metabolic disorders (e.g., obesity, elevated blood sugar, diabetes, fatty liver disease, PCOS, and multiple sclerosis) by administering PYY and PYY analog formulations to a subject, and reducing symptoms associated with the metabolic disorders compared to a subject that has not received PYY or PYY analog formulations.

Yet another aspect provides methods of increasing a feeling of fullness in a subject by administering a PYY or a PYY analog formulation to the subject, for example, before a meal. In this aspect, the feeling of fullness can last at least about 30, 60, 90, or 120 minutes or longer after the PYY or PYY analog formulation is administered to subject and after the subject has eaten a meal. In another aspect, the pharmaceutical composition is administered to the subject, and the subject subsequently consumes a meal.

DETAILED DESCRIPTION

Figure 1:
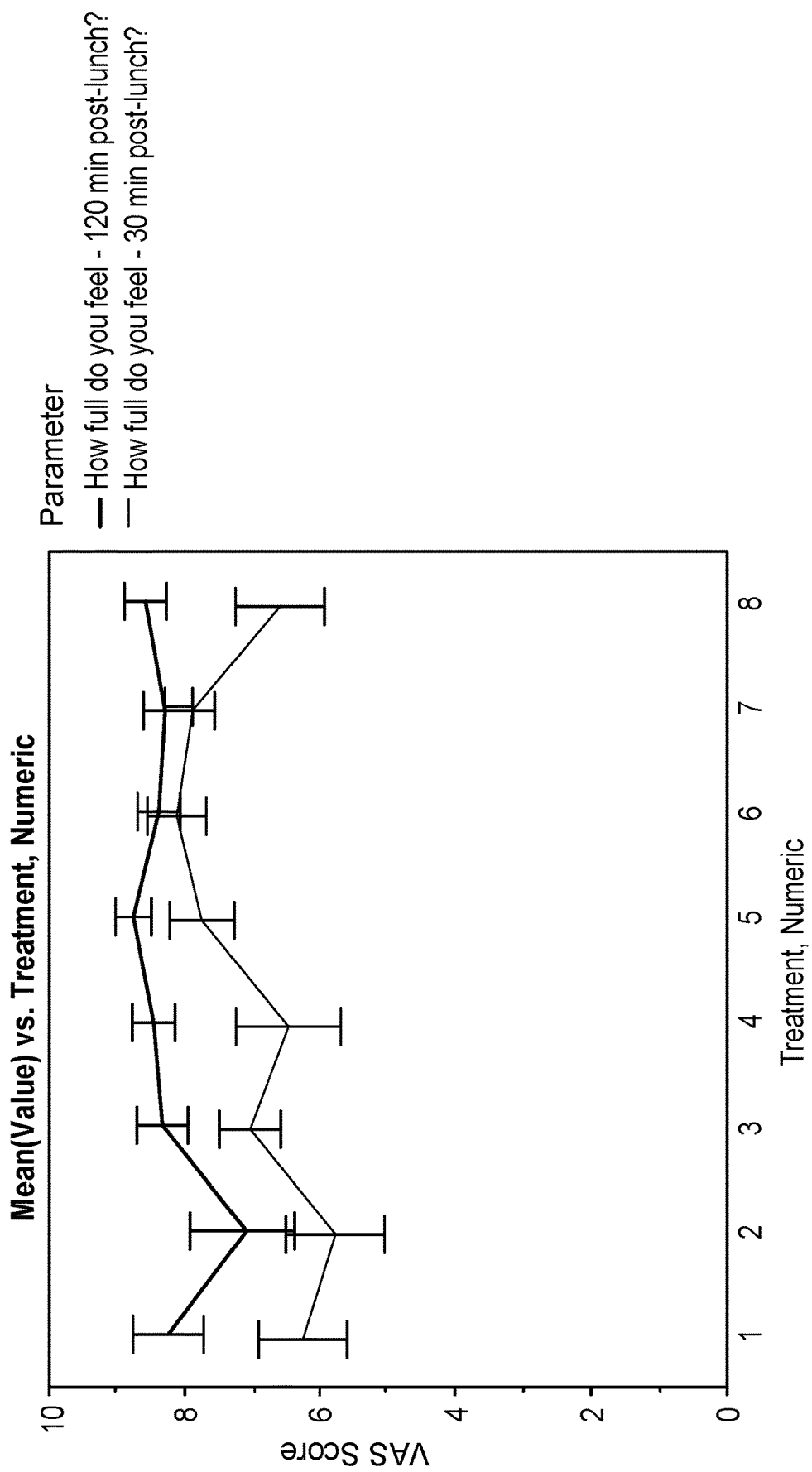
FIG. 1 shows the results of an exemplary study where PYY(3-36) was administered intraorally to subjects at the indicated dose (GT-001 Dose on the x-axis), and a feeling of fullness (mean value on y-axis) was assessed 30 minutes and 120 minutes after the subjects ate lunch.

Before describing an exemplary aspect described herein, it is to be understood that the invention is not limited to the details of construction or process steps set forth in the following description. The aspects described herein are capable of being practiced or being carried out in various ways.

Satiation occurs during a meal. It's that point at which a subject feels that she has had enough to eat, and does not desire any more food. Satiety, on the other hand, describes a subject's experience after a meal—how long before the subject starts to feel hungry again. A "feeling of fullness" refers to an indicator of satiety as reported by a person following the eating of food or a meal. The degree and duration of a feeling of fullness (satiation and satiety) are predictor of whether a person will continue to eat or resume eating and therefore increase caloric intake over time. Thus, increasing the degree and duration of a feeling of fullness reduces overall caloric intake and a reduction in weight and obesity.

A Visual Analogue Scale (VAS) is an instrument, tool, or methodology used to measure a characteristic that can vary in value or degree, and is otherwise not easily subject to direct measurement. For example, a VAS is often used to determine the degree of pain suffered by a patient (e.g., a scale of 1 to 10). Likewise, a VAS can be used reliably to measure the degree of fullness reported by a subject following the eating of food or a meal. See, e.g., Blundell et al., "Appetite Control: Methodological Aspects of The Valuation of Foods," Obes Rev. 2010 March; 11(3): 251-270; Flint et al., "Reproducibility, power and validity of visual analogue scales in assessment of appetite sensations in single test meal studies," International Journal of Obesity (2000) 24, 38-48 (2000).

Metabolic disorders, diseases, or metabolic syndrome refers to diseases or conditions that increase risk for diseases or disorders associated with, related to, or caused by abnormal metabolism (e.g., diabetes, heart disease, stroke, obesity, elevated blood sugar, fatty liver disease, PCOS (polycystic ovary syndrome), and multiple sclerosis). The lack of effective long term, non-invasive procedures for metabolic disorders has spurred the search for small molecules capable of treating these conditions with minimal side effects. While several small molecule therapeutics are currently on the market, their efficacy is relatively low, and safety profiles are less than ideal. On the other hand, natural human hormones responsible for regulation of hunger, satiety and energy metabolism in normal physiology, and their analogs, as described herein, can be used to treat such diseases.

GLP-1 receptor agonists, and PYY(3-36) and analogs have been used with limited success in treating metabolic disorders. Therapeutic outcomes with GLP-1 receptor agonists for diabetes mellitus (DM) and obesity are highly variable, and result in significant side effects. While PYY (3-36) is a strong inducer of satiety, systemically administered PYY and analogs tend to be associated with severe side effects, such as nausea and vomiting.

Aspects described herein provide compositions comprising PYY and PYY analogs such as PYY(3-36). In certain aspects, these compositions can be used to treat metabolic diseases (e.g., obesity, diabetes, elevated blood sugar, etc.). These compositions can be used to reduce, ameliorate, or treat conditions in patients more effectively than simple aqueous solutions or simple dry compositions.

In one aspect, the term "PYY(3-36)" or "native PYY-3-36" refers to amino acids 3-36 of the human PYY molecules, having the following amino acid sequence (from amino to carboxy terminus):

(SEQ ID NO: 1)
{NH2}-ILE-LYS-PRO-GLU-ALA-PRO-GLY-GLU-ASP-ALA-

SER-PRO-GLU-GLU-LEU-ASN-ARG-TYR-TYR-ALA-SER-LEU-

ARG-HIS-TYR-LEU-ASN-LEU-VAL-THR-ARG-GLN-ARG-TYR-

{COOH}.

Native PYY(3-36) is post-translationally processed from a precursor peptide encoded by the following mRNA nucleic acid sequence (positions 632-733 (bolded below)) encode the mature peptide):

```
                                                          (SEQ ID NO: 2)
   1 gcccctggag gaactgaacc cactatcggt catggggccg agactaaatg tggcgggttg 61 tctttaatct gctgccaaga ggaaactcat tcaggcaagt tcagcccttt atgaggaatt 121 ccectgtggt cacattccaa ttcctggacc tgctgccacc ctcagaactg catgctcctt 181 cttcagactt tctaagaatg actcaggtca ttggtggagt gaagtcaaga tttccaactc 241 agtcacctga agagatggag ataccattca tggagctgga ggtccctgga gatttgggaa 301 ttcagataac aagctaagat aaggagtttg cctacctctg tcctagagcg aagcctgagc 361 cttgggcgcg cagcacacca caagtatctg ttactgtgtt ttgcagaagc ttcaggcggg 421 gatataagcc ccacaaggaa agcgctgagc agaggaggcc tcagcttgac ctgcggcagt 481 gcagcccttg ggacttccct cgccttccac ctcctgctcg tctgcttcac aagctatcgc 541 tatggtgttc gtgcgcaggc cgtggcccgc cttgaccaca gtgcttctgg ccctgctcgt 601 ctgcctaggg gcgctggtcg acgcctaccc catcaaaccc gaggctcccg gcgaagacgc 661 ctcgccggag gagctgaacc gctactacgc ctccctgcgc cactacctca acctggtcac 721 ccggcagcgg tatgggaaaa gagacggccc ggacacgctt ctttccaaaa cgttcttccc 781 cgacggcgag gaccgccccg tcaggtcgcg gtcggagggc ccagacctgt ggtgaggacc 841 cctgaggcct cctgggagat ctgccaacca cgcccacgtc atttgcatac gcactcccga 901 ccccagaaac ccggattctg cctcccgacg gcggcgtctg ggcagggttc gggtgcggcc 961 ctccgcccgc gtctcggtgc ccccgccccc tgggctggag ggctgtgtgt ggtccttccc 1021 tggtcccaaa ataaagagca aattccacag aaacggaaaa aaaaaaaaa
```

In another aspect, the term "PYY(3-36)" further comprises analogs or variants of native PYY(3-36) that retain at least about 20, 30, 40, 50, 60, 70, 80, 90 or 100% of the biological activity of native PYY(3-36). In this aspect, term "variants" refers to modifications to or substitutions of one or more amino acids of native PYY(3-36). Substitution of an amino acid refers to replacement of one amino acid with another amino acid. In one aspect, an amino acid may be replaced with an amino with a similar side group (e.g., acidic, basic, neutral). The term "biological activity" refers to the activation of Y receptors by one or more small molecules described herein, producing an effect, either locally or systemically, on food intake, gastrointestinal function or central nervous system activity.

Analogs or variants of PYY(3-36) include, for example, the analogs or variants of PYY. See, e.g., Michel et al., *Dipeptidyl peptidase IV inhibitors in diabetes; more than inhibition of glucagon-like peptide-1 metabolism*? Naunyn-Schmiedeberg's Arch Pharmacol (2008) 377:205-207; Niida et al., *Antiobesity and emetic effects of a short-length peptide YY analog and its PEGylated and alkylated derivatives*, Bioorganic & Medicinal Chemistry (2017) (S0968-0896 (Epub ahead of print). In one aspect, these analogs and variants can be used in the pharmaceutical compositions described herein.

Aspects described herein provide pharmaceutical compositions comprising PYY, wherein the dose of PYY provided to a subject is at least about 2.5 ng when the PYY is administered to the subject. In another aspect, PYY is PYY(3-36). In yet another aspect, the dose of PYY, PYY (3-36), or other PYY analogs is about 25 ng, 250 ng, 2.5 µg, 25 µg, 250 µg, or 2.5 mg. In further aspects, the dose of PYY, PYY(3-36), or other PYY analogs can range from about 25 ng to about 2.5 mg, from about 250 ng to about 250 µg, or from about 2.5 µg to about 25 µg.

Further aspects provide a pharmaceutical composition, comprising a satiety peptide in a dose of about 2.5 ng to about 2.5 mg, and a pharmaceutically acceptable excipient. In another aspect, the pharmaceutical composition of claim 23, wherein the satiety peptide is selected from the group consisting of GLP-1, oxyntomodulin, and cholecystokinin.

In another aspect, the dose per volume of PYY(3-36) can range, for example, from about 2.5 ng to about 250 µg in a volume from about 25 µl to about 5 mls of solvent (e.g., water, buffer, etc.). In another aspect, the dose/volume is about 2.5 µg/ml. In another aspect, the dose/volume is about 500 µg/500 µl. The volume of a pharmaceutical formulation selected for delivering a dose of PYY(3-36) can be selected, for example, to optimize the residency time of PYY(3-36) in the oral cavity and, more specifically, the tongue in order to increase the interaction between PYY(3-36) and its receptor on the tongue (e.g., Y2 receptor).

Further aspects comprise these pharmaceutical compositions comprising nucleotides encoding or peptides having substantial identity to PYY, PYY(3-36), or other PYY analogs in addition to one or more of the following, or with one or more of the following in place of PYY, PYY(3-36), or other PYY analogs: GLP-1, oxyntomodulin, and cholecystokinin acetyl-CoA carboxylase-(ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, GLP-1 receptor agonists, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors, inhibitors or modulators of PDHK2 or PDHK4, inhibitors of MAP4K4, modulators of IL1 family including IL1beta, HMG-CoA reductase inhibitors, squalene synthetase inhibitors, fibrates, bile acid sequestrants, ACAT inhibitors, MTP inhibitors, lipooxygenase inhibitors, cholesterol absorption inhibitors, PCSK9 modulators, cholesteryl ester transfer protein inhibitors and modulators of RXRα, GIP receptor agonists, enterostating and enterostatin analogs, amylin and amylin receptor agonists, ghrelin modulators (e.g., inhibitors) and leptin and leptin receptor agonists, pancreatic polypeptide (PP), calcitonin, OXM, neuropeptide Y (NPY), human growth hormone, prolactin, oxytocin, bovine growth hormone, porcine growth hormone, ghrelin, ghrelin receptor antagonists, and glucagon and analogs and variants thereof.

In yet another aspect, pharmaceutical compositions comprising one or more active pharmaceutical ingredients selected from the group consisting of PYY, PYY(3-36), GLP-1, oxyntomodulin, and cholecystokinin, acetyl-CoA carboxylase-(ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, GLP-1 receptor agonists, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors, inhibitors or modulators of PDHK2 or PDHK4, inhibitors of MAP4K4, modulators of IL1 family including IL1beta, HMG-CoA reductase inhibitors, squalene synthetase inhibitors, fibrates, bile acid sequestrants, ACAT inhibitors, MTP inhibitors, lipooxygenase inhibitors, cholesterol absorption inhibitors, PCSK9 modulators, cholesteryl ester transfer protein inhibitors and modulators of RXRα, GIP receptor agonists, enterostating and enterostatin analogs, amylin and amylin receptor agonists, ghrelin modulators (e.g., inhibitors) and leptin and leptin receptor agonists, pancreatic polypeptide (PP), calcitonin, OXM, neuropeptide Y (NPY), human growth hormone, prolactin, oxytocin, bovine growth hormone, porcine growth hormone, ghrelin, ghrelin receptor antagonists, and glucagon and a pharmaceutically acceptable excipient. In this aspect, these active ingredients can be formulated at therapeutic doses, and if the second drug is PYY or PYY(3-36), its dose can be at from about 2.5 ng to about 2.5 mg. The term "therapeutic dose" refers to a dose at which a pharmaceutically active ingredient can treat, ameliorate, or reduce symptoms associated with a disease, disorder, or condition.

In another aspect, these pharmaceutical compositions further comprise pharmaceutically acceptable excipients (e.g., propylene glycol, potassium sorbate, 1-arginine, edetate disodium, monosodium phosphate, and polysorbate 20). In one aspect, propylene glycol is present in a concentration of about 100 mg/ml, 1-arginine is present in a concentration of about 25 mg/ml, potassium sorbate is present in a concentration of about 2 mg/ml, edetate disodium is present in a concentration of about 1.2 mg/ml, sodium phosphate monobasic dihydrate is present in a concentration of about 7.8 mg/ml, and polysorbate is present in a concentration of about 5 mg/ml. Further aspects comprise these pharmaceutical compositions with GLP-1, oxyntomodulin, and cholecystokinin in place of PYY, PYY(3-36), or other PYY analogs and variants.

For example, the pharmaceutical compositions described herein can include co-solvent stabilizers like propylene glycol or other suitable co-solvent stabilizers (e.g., lower molecular weight polyethylene glycols (PEG) such as PEG 200 and 400, glycerin, and ethanol (alcohol)).

In another aspect, the pharmaceutical compositions described herein can include amino acid stabilizers like L-Arginine or other suitable amino acid stabilizers (e.g., alanine, arginine, aspartic acid, glycine, lysine, proline, and methionine).

In yet another aspect, the pharmaceutical compositions described herein can include preservatives like potassium sorbate, or other suitable preservatives (e.g., ascorbic acid, benzyl alcohol, benzoic acid, citric acid, chlorobutanol, m-cresol, glutathione, methionine, methylparaben, propylparaben, sodium sulfite, parahydroxybenzoate esters (methylhydroxybenzoate and propylhydroxybenzoate), boric acid and borate salts, sorbic acid and other sorbate salts besides potassium, and phenolics)).

In another aspect, the pharmaceutical compositions described herein can include antioxidants such as edetate disodium or another suitable antioxidant (e.g., sodium formaldehyde sulphoxylate, butylated hydroxyanisole, and butylated hydroxytoluene). In another example, the pharmaceutical compositions described herein can include buffers like phosphate or other suitable buffers (e.g., acetate, carbonate, citrate, citrate-phosphate, glycine, HEPES, histidine, maleate, phosphate, succinate, tartrate, and triethanolamine (Tris)). In another example, the pharmaceutical compositions described herein can include surfactants like polysorbate 20 or other suitable surfactants (e.g., Poloxamer 188/407, polysorbate 40 or 80, or sodium lauryl sulfate).

In yet another aspect, the excipients include flavorings to increase compliance with ingesting the pharmaceutical formulation. For example, the flavorings can be used to mask bitter or other undesirable flavor properties, or to make the pharmaceutical formulation compatible with the flavor of food that may be ingested before or after the pharmaceutical formulations. Compatible flavorings include, for example, apple, banana; bubblegum, cherry, chocolate, grape, lemon, mango, orange, raspberry, strawberry, vanilla, watermelon, mint or a combination of the above flavors. In another aspect, these flavorings are dye-free, sugar-free, hypoallergenic, gluten-free, and casein-free.

In one aspect, the pharmaceuticals compositions described herein are adapted for delivery to the oral cavity (e.g., intraoral, oromucosal, transmucosal, topical lingual, gargles, mouthwashes, gingival solutions, oromucosal solutions and oromucosal suspensions, semi-solid oromucosal preparations (including for example gingival gel, gingival paste, oromucosal gel, oromucosal paste)), oromucosal drops, oromucosal sprays and sublingual sprays (including oropharyngeal sprays), dry powder sprays, lozenges and pastilles, compressed lozenges, sublingual tablets and buccal tablets, oromucosal capsules, mucoadhesive preparations)). See, e.g., Oromucosal Preparations, (Ph Eur monograph 1807). In another aspect, the PYY in the pharmaceutical composition is adapted for binding to the Y2 receptor.

The term "adapted for delivery" refers to a pharmaceutical formulation or ingredient that has properties or is configured to be preferentially delivered or bound to a desired area of the body (e.g., mouth, tongue) or a target (e.g., a receptor). The term "adapted for delivery to the oral cavity" refers to a pharmaceutical formulation that can preferentially deliver PYY(3-36) to the oral cavity or, more specifically, the tongue or one or more active substances intended for administration to the oral cavity and/or the throat to obtain a local or systemic effect. See, e.g., Oromucosal Preparations, (Ph Eur monograph 1807). The term "adapted for binding to a receptor" or "adapted for binding to the Y2 receptor," refers to a satiety peptide, analog, or other active ingredient that has a binding affinity to the Y2 receptor or residence time on the tongue sufficient to induce satiety (e.g., about 30 seconds to about 1 min). In one aspect, "local oral delivery" can refer to obtaining a local effect without increasing the levels of an active ingredient in the blood plasma.

The excipients in such a pharmaceutical formulation are compatible with the mouth for intraoral delivery, and the active ingredient in the pharmaceutical formulation can maintain its activity in the mouth until delivered to its site of activity. In another aspect, PYY(3-36) is delivered to the tongue, and binds to a Y receptor (e.g., the Y2 receptor).

In this aspect, PYY(3-36) can bind to the tongue, and transmit a signal to the brain via a receptor (e.g., Y2 receptor). In another aspect, PYY(3-36) can be delivered systemically by any suitable route of administration (e.g., oral, parenteral, intravenous, etc.).

The term "binds" refers to an association between PYY (3-36) (or other satiety peptides and metabolic hormones as described herein) or a portion of the PYY(3-36) molecule, and a Y receptor through a chemical bond (e.g., ionic, covalent, or hydrophobic) or other chemical or physical attraction between PYY(3-36) or a portion thereof and a Y receptor where a biological response is induced by the association between PYY(3-36) and the Y receptor. See e.g., Doods, *Receptor binding profiles of NPY analogues and fragments in different tissues and cell lines*, Peptides. 1995; 16(8):1389-94.

In another aspect, the pharmaceutical compositions comprise excipients that increase the time PYY(3-36) is in contact with the mucosa (e.g., viscosity enhancement, encapsulation, and controlled release). Without being bound by theory, it is believed that increasing the contact time of the pharmaceutical formulation with the mucosa, leads to increased binding of PYY(3-36) to its receptor on the tongue. Suitable excipients for viscosity enhancement include rheology modifiers which also may be mucoadhesive such as methylcellulose, hydroxyethylcellulose, hydroxypropylcellulose, alginic acid, polyvinylpyrrolidone, and sodium carboxymethylcellulose. Suitable excipients for modified release of the PYY(3-36) in the oral cavity include mucoadhesive permeation enhancers such as 23-lauryl ether, aprotinin, azone, benzalkonium chloride, cetylpyridinium chloride, cetyltrimethylammonium bromide, cyclodextrins, dextran sulfate, and lauric acid. Other suitable mucoadhesive polymers used for buccal or intraoral delivery include agarose, chitosan, gelatin, hyaluronic acid, gums (e.g. guar, hakea, xanthan, gellan, carrageenan, pectin, and sodium alginate), cellulose derivatives (e.g., CMC, thiolated CMC, sodium CMC, HEC, HPMC, MC, methylhydroxylethylcellulose), poly (acrylic acid)-based polymers (e.g., CP, PC, PAA, polyacrylates, poly(methylvinylether-co-methacrylic acid), poly(2-hydroxyethyl methacryalate), poly(alkylcyanoacryalate), poly(isohexylcyanocrylate), poly(isobutylcyanoacrylate), copolymer of acrylic acid and PEG, poly(N-2-hydroxypropyl methacrylamide), PHPMAm, polyoxyethylene, PVA, PVP, and other thiolated polymers; scleroglucan, PVA, steroidal detergents, non-ionic surfactants, laureth-9, sodium fusidate, included sodium lauryl, sodium laurate (e.g., pH 8.9), palmitoyl carnitine, lauric acid/propylene glycol vehicle, Brij 78, sodium deoxycholate, sodium lauryl sulfate, lecithin and PVP. See, e.g., International Journal of Pharmaceutics, Volume 53, Issue 3, 1 Aug. 1989, Pages 227-235.

In another aspect, the pharmaceutical compositions comprise excipients that increase the residence time of PYY(3-36) in the saliva (e.g., the amount of time PYY(3-36) remains in the saliva without significant degradation of the peptide). Without being bound by theory, it is believed that increasing the residence time of PYY(3-36) in the saliva increases the opportunity for PYY(3-36) to bind its receptor on the tongue. The residence time in the saliva can optionally be adjusted to avoid increasing systemic exposure to PYY(3-36) through, for example, swallowing.

The term "pharmaceutically acceptable excipients" includes, for example:
(1) Stabilizers (e.g., co-solvents like propylene glycol, polyethylene glycols (PEG), glycerin, and ethanol (alcohol)) and amino acids (e.g., alanine, L-Arginine, arginine, aspartic acid, glycine, lysine, proline, and methionine).
(2) Preservatives (e.g., potassium sorbate, ascorbic acid, benzyl alcohol, benzoic acid, citric acid, chlorobutanol, m-cresol, glutathione, methionine, methylparaben, propylparaben, sodium sulfite, parahydroxybenzoate esters (methylhydroxybenzoate and propylhydroxybenzoate), boric acid and borate salts, sorbic acid and sorbate salts, and phenolics).
(3) Antioxidants (e.g., edetate disodium, sodium formaldehyde sulphoxylate, butylated hydroxyanisole, and butylated hydroxytoluene);
(4) Buffers (e.g., phosphate, acetate, carbonate, citrate, citrate-phosphate, glycine, HEPES, histidine, maleate, phosphate, succinate, tartrate, and triethanolamine (Tris));

(5) Surfactants (e.g., polysorbate 20, poloxamer 188/407, polysorbate 20/40/80, and sodium lauryl sulfate);

(6) Rheology modifiers (e.g., methylcellulose, hydroxyethylcellulose, hydroxypropylcellulose, alginic acid, polyvinylpyrrolidone, and sodium carboxymethylcellulose);

(7) Mucosal Permeation Enhancers (e.g., 23-lauryl ether, aprotinin, azone, benzalkonium chloride, cetylpyridinium chloride, cetyltrimethylammonium bromide, cyclodextrin, dextran sulfate, and lauric acid);

(8) Excipients used to stabilize active ingredients in lyophilized tablets for oral disintegration and dissolution in the oral cavity including sugars or sugar alcohols such as sucrose, trehalose, mannitol, dextrose, and polyvinylpyrrolidone (PVP) or glycine;

(9) Flavorings like apple, banana, bubblegum, cherry, chocolate, grape, lemon, mango, orange, orange swirl, raspberry, strawberry, strawberry swirl, vanilla, walberry swirl, and watermelon (including dye-free, sugar-free, hypoallergenic, gluten-free, and casein-free versions); and sweetening agents, including sucrose, liquid glucose, glycerol, sorbitol, saccharin sodium and aspartame); and In one aspect, delivery of PYY(3-36) compositions to the tongue minimizes or eliminates any substantial systemic delivery of PYY(3-36). The term "substantial systemic delivery" refers to blood levels of administered PYY(3-36) or its analogs or variants that exceed the limit of detection, are distinguishable from circulating levels, or cause a significant increase in circulating levels.

Further aspects provide methods of treating metabolic disorders or diseases in a subject. In another aspect, the metabolic disease can be selected from the group consisting of obesity, elevated blood sugar (e.g., elevated blood sugar levels), diabetes, fatty liver disease, high blood pressure, PCOS, and multiple sclerosis. In these aspects, "treatment" or "treat" refers to administering PYY (e.g., PYY(3-36)) or another PYY analog) to a patient having the indicated metabolic disease.

When the metabolic disorder is obesity, food intake by the subject is reduced by at least about 20% in the subject after treatment with a dose of the pharmaceutical composition compared to a subject who did not receive treatment. In another aspect, body weight of the subject is reduced by at least about 5% after treatment with a dose of the pharmaceutical composition compared to a subject who did not receive treatment. In the aspects described herein, the term "subject" refers to an animal (e.g., human, non-human) in need of treatment for the indicated disease or condition.

When the metabolic disorder is elevated blood sugar (e.g., pre-diabetes), the blood sugar or glucose levels of a subject is reduced by at least about 10% after treatment with a dose of the pharmaceutical composition compared to a subject who did not receive treatment. In another aspect, the fasting glucose level is reduced by at least about 10% after treatment with a dose of the pharmaceutical composition compared to a subject who did not receive treatment.

When the metabolic disease is disorder, the area under the curve (AUC) in a glucose tolerance test of a subject is reduced by at least about 15% after treatment with a dose of the pharmaceutical composition compared to a subject who did not receive treatment. In another aspect, HbA1c levels in a subject are reduced by at least about 15% after treatment with a dose of the pharmaceutical composition compared to a subject who did not receive treatment.

When the metabolic disorder is fatty liver disease, the liver fat concentration in a subject is reduced by about 20% after treatment with a dose of the pharmaceutical composition compared to a subject who did not receive treatment. In this aspect, liver fat concentration can be measured by, for example, liver biopsy, ultrasound, MRI (magnetic resonance imaging), and elastography.

When the metabolic disorder is PCOS, PCOS symptoms in a subject are reduced by at least about 15 to 20% after a dose of the pharmaceutical composition compared to a subject who did not receive the dose. In this aspect, the exemplary symptoms include, but are not limited to, hormonal profile (e.g., thyroid function tests, serum prolactin levels, and a free androgen index (defined as total testosterone divided by sex hormone binding globulin [SHBG]×100, to give a calculated free testosterone level), LH2FsH ratio, and testosterone level).

When the metabolic disorder is multiple sclerosis (MS), multiple sclerosis symptoms are reduced in a subject by at least about 20% after treatment with a dose of the pharmaceutical composition compared to a subject who did not receive treatment. In this aspect, the symptoms include, but are not limited to, the Multiple Sclerosis Functional Composite. See, e.g., Cutter et al., *Development of a multiple sclerosis functional composite as a clinical trial outcome measure*, Brain, 1999 May; 122 (Pt 5):871-82.

When the metabolic disorder is high blood pressure, systolic and diastolic blood pressure levels in a subject are reduced by at least about 20% after treatment with a dose of the pharmaceutical composition compared to a subject who did not receive treatment. In this aspect, for example, treatment can be started when systolic and diastolic blood pressure levels of 140 mm Hg or greater or at diastolic levels of 90 mm are reached.

The term "metabolic disorder" refers to a human or animal condition or disease resulting from abnormal function or control of the metabolic system (e.g., obesity, diabetes, fatty liver disease, PCOS, and elevated blood glucose levels). The term "disorder" generally refers to disruption to regular bodily structure and function or a pathophysiological response to internal or external factors.

Further aspects provide methods of increasing a feeling of fullness in a subject comprising administering the pharmaceutical compositions described herein to the subject. In this aspect, the dose of PYY, PYY(3-36) or a variant or analog can be about 25 ng, 250 ng, 2.5 μg, 25 μg, 250 μg, or 2.5 mg. In further aspects, the dose of PYY, PYY(3-36) or a variant or analog can range from about 25 ng to about 2.5 mg, from about 250 ng to about 250 μg, or from about 2.5 μg to about 25 μg. In yet another aspect, the feeling of fullness in the subject can last at least 30, 60, 90, or 120 minutes after treatment and after eating a meal. In another aspect, the pharmaceutical composition is administered to the subject, and the subject subsequently consumes a meal.

In this aspect, the dose per volume of PYY(3-36) can range, for example, from about 2.5 ng to about 250 μg in a volume from about 25 μl to about 5 mls. In another aspect, the dose/volume is 2.5 μg/ml. In another aspect, 500 μg/500 μL. The volume of a pharmaceutical formulation selected for delivering a dose of PYY(3-36) can be selected, for example, to optimize the residency time of PYY(3-36) in the oral cavity and, more specifically, the tongue in order to increase the interaction between PYY(3-36) and its receptor on the tongue (e.g., Y2 receptor).

The term "eating a meal" refers a subject eating food with a total caloric intake of at least about, for example, 300-2000, 500-1000 calories, or 300-800 calories. The term "feeling of fullness" refers to a subject self-reporting satiety following eating a meal as measured using, for example, VAS measurement wherein the VAS measurement is increased by at least about 10%. In another aspect, the VAS measure is increased by at least about 20%. In another aspect, a functional magnetic resonance imaging ("fMRI") scan before and after treatment can be used to measure a feeling of fullness (by measuring blood flow changes in specific regions of the brain, for example the satiety centers of the brain stem, such as the nucleus tractus solitaris, and the hypothalamus, such as the lateral hypothalamic area). In yet another aspect, subjects can verbally report a level of feeling of fullness before and after treatment. In yet another aspect, subjects can verbally report a level of feeling of fullness before and after treatment.

In one aspect, the pharmaceutical compositions comprising PYY(3-36) can be delivered to a subject in need of treatment before, after, or during a meal. In this aspect, the pharmaceutical compositions can be delivered intraorally.

In one aspect the composition can be incorporated in any suitable dosage form (e.g., a lozenge, a dissolvable material, a dissolvable planar sheet, chewing gum, or a solid or semi-solid candy). In another aspect, the composition can be incorporated in a liquid formulation (e.g., emulsion, a syrup, an elixir, a suspension, or a solution). In a further aspect, the composition can be incorporated in a spray for oral administration, or drops for oral administration.

In one aspect, the pharmaceutical composition is as follows:

TABLE 1

Exemplary PYY(3-36) Pharmaceutical Formulation

| Component and Quality Standard | Function | Quantity per unit (mg/mL) | Strength (label claim) % |
|---|---|---|---|
| $PYY_{3-36}$, human | Drug substance | 2.5 ng/mL to 2.5 mg/mL | $2.5 \times 10^{-7}$ to 0.25% |
| Propylene Glycol, USP | Stabilizer | 100 | 10 |
| L-Arginine, Free Base, USP | Stabilizer | 25 | 2.5 |
| Potassium Sorbate, NF | Preservative | 2 | 0.20 |
| Edetate Disodium, Dihydrate, USP | Antioxidant | 1.2 | 0.12 |
| Sodium Phosphate, Monobasic, Dihydrate, USP | Buffer | 7.8 | 0.78 |
| Polysorbate 20, NF | Surfactant | 5 | 0.50 |
| Hydrochloric Acid (HCl), NF, USP | pH modifier | QS to pH 7.0 ± 0.1 | |
| Sodium Hydroxide (NaOH), USP | pH modifier | QS to pH 7.0 ± 0.1 | |
| Sterile Water for Injection, USP | Solvent | QS to 1 mL | QS to 100% |

An exemplary clinical trial was performed as a dose-escalation design trial. Approximately twelve evaluable subjects (n~12) with BMIs of 30 to 40 kg/m² received a single dose of placebo followed by study drug (PYY(3-36) also known as GT-001) applied directly to the surface of the lingual mucosa with a disposable pipette followed by a one-day washout. A total of seven (7) doses was escalated to a dose of 2.5 mg/ml.

Without being bound by theory, it is believed that food intake is regulated by two opposing mechanisms; appetite and satiation. Both mechanisms are regulated by the brain-gut axis. A fasting period induces appetite by secretion of ghrelin from the stomach. Ghrelin acts on specialized neurons in the arcuate nucleus of the hypothalamus to activate the agouti-related peptide/NPY (AgRP/NPY) pathway. The AgRP/NPY pathway is responsible for stimulating appetite centers in the cerebral cortex that prepare the gastrointestinal tract for food intake and stimulate food-seeking behavior. Food intake then stimulates secretion of satiation hormones in the gut including PYY(3-36), oxyntomodulin, and glucagon-like peptide-1 (GLP-1). These hormones stimulate the pro-opiomelanocortin/alpha-melanocyte stimulation hormone (POMC/αMSH) pathway. The POMC/αMSH pathway stimulates different receptors in the cerebral cortex to produce a sensation of satiation and food reward (Acosta et al., 2014).

It was recently demonstrated that PYY(3-36) is also present in both murine and human saliva. In mice, salivary PYY(3-36) derives from both plasma and is also synthesized in the taste cells in taste buds of the tongue [2]. Moreover, the cognate receptor, Y2R, is expressed in the tongue epithelia (Acosta, et al. 2011; Hurtado et al., 2012). In addition, all other YRs (Y1R, Y4R, and Y5R) are abundantly expressed in multiple lingual cell types, including epithelial progenitors, keratinocytes, neuronal dendrites and taste receptor cells (TRCs) (Hurtado et al., 2012). We showed that PYY expressed in TRCs modulates responsiveness to bitter-tasting stimuli and to lipids (La Sala, FASEB, 2013).

Previous results demonstrated that augmentation of salivary PYY(3-36) or Exendin-4 result in a decrease in 1-hour food intake (Acosta et al., 2011). The effect is peptide-specific; similar studies with neuropeptide Y or amylin resulted in no effect on food intake. Moreover, it was shown that there is a dose-response effect. At the lower dose, 0.3 µg/100 g PYY(3-36), treated mice reduced their caloric intake by 16% as compared to controls. (PYY(3-36) 3.44±0.06 kcal vs. vehicle 4.10±0.04 kcal, p=0.01) At the intermediate dose, 3 µg/100 g PYY(3-36), the reduction was 26%. (PYY(3-36) 3.01±0.06 kcal vs. vehicle 4.10±0.04 kcal, p=0.008). At the higher dose, 10 µg/100 g PYY(3-36), the caloric intake was further reduced by 42%. (PYY(3-36) 2.36±0.05 kcal vs. vehicle 4.10±0.04 kcal, p=1.81E-06) (Acosta et al., 2011). However, the doses of PYY used in these studies are significantly higher than described in aspects herein and could result in undesired side effects and lack of efficacy (e.g., tachiphylaxsis—loss of response at higher doses) in humans.

The effects of PYY are mediated through the activation of specific Y2 receptors expressed on the lingual epithelial cells. In a long-term study involving diet-induced obese (DIO) mice, a sustained increase in PYY(3-36) was achieved using viral vector-mediated gene delivery targeting salivary glands (Acosta et al., 2014). The chronic increase in salivary PYY(3-36) resulted in a significant long-term reduction in food intake and body weight. Augmentation of salivary PYY(3-36), while reliably inducing strong anorexic responses, does not cause taste aversion, a surrogate of nausea in rodents (Hurtado et al., 2013). Salivary PYY(3-36) activated forebrain areas known to mediate feeding, hunger, and satiation while minimally affecting brainstem chemoreceptor zones that trigger nausea. By comparing neuronal pathways activated by systemic versus salivary PYY(3-36), a metabolic circuit was identified associated with Y2R-positive cells on the tongue and extending through brainstem nuclei into hypothalamic satiety centers.

In accordance with aspects disclosed herein, this alternative circuit regulates ingestive behavior (e.g., promotes a feeling of fullness over time) without inducing taste aversion. Aspects described herein provide PYY (e.g., PYY(3-36)) formulations for the treatment of obesity via direct lingual application and without concomitant nausea.

TABLE 2

Dose Escalation Study

| Study Visit Day | DOSE of PYY(3-36) | DOSE PYY(3-36) in 1 ml |
|---|---|---|
| Day 1 | placebo | placebo |
| Day 2 | 2.5 × E−6 mg | 2.5 × E−3 µg |
| Day 4 | 2.5 × E−5 mg | 2.5 × E−2 µg |
| Day 6 | 2.5 × E−4 mg | 2.5 × E−1 µg |
| Day 8 | 2.5 × E−3 mg | 2.5 µg |
| Day 10 | 2.5 × E−2 mg | 25 µg |
| Day 12 | 2.5 × E−1 mg | 250 µg |
| Day 14 | 2.5 mg | 2.5 mg |

Table 2 shows an exemplary dose-escalation study from Day 1 through Day 14 with two day intervals between doses after Day 2. The dose can be prepared, for example, from a stock solution of 2.5 mg/ml PYY(3-36).

FIG. 1 shows the results of an exemplary study where PYY(3-36) in 12 subjects. PYY(3-36) was administered to subjects at the indicated dose (GT-001 Dose on the x-axis), and a feeling of fullness (mean value on y-axis) was assessed by VAS 30 minutes and 120 minutes after lunch. As shown in FIG. 1, the feeling of fullness is significantly above placebo level at a dose of 25 ng at 120 minutes post-lunch (VAS score of 7), increases at a dose of 2.5 µg, and reaches about 8 on the VAS scale at a dose of 250 µg.

Figure 2:
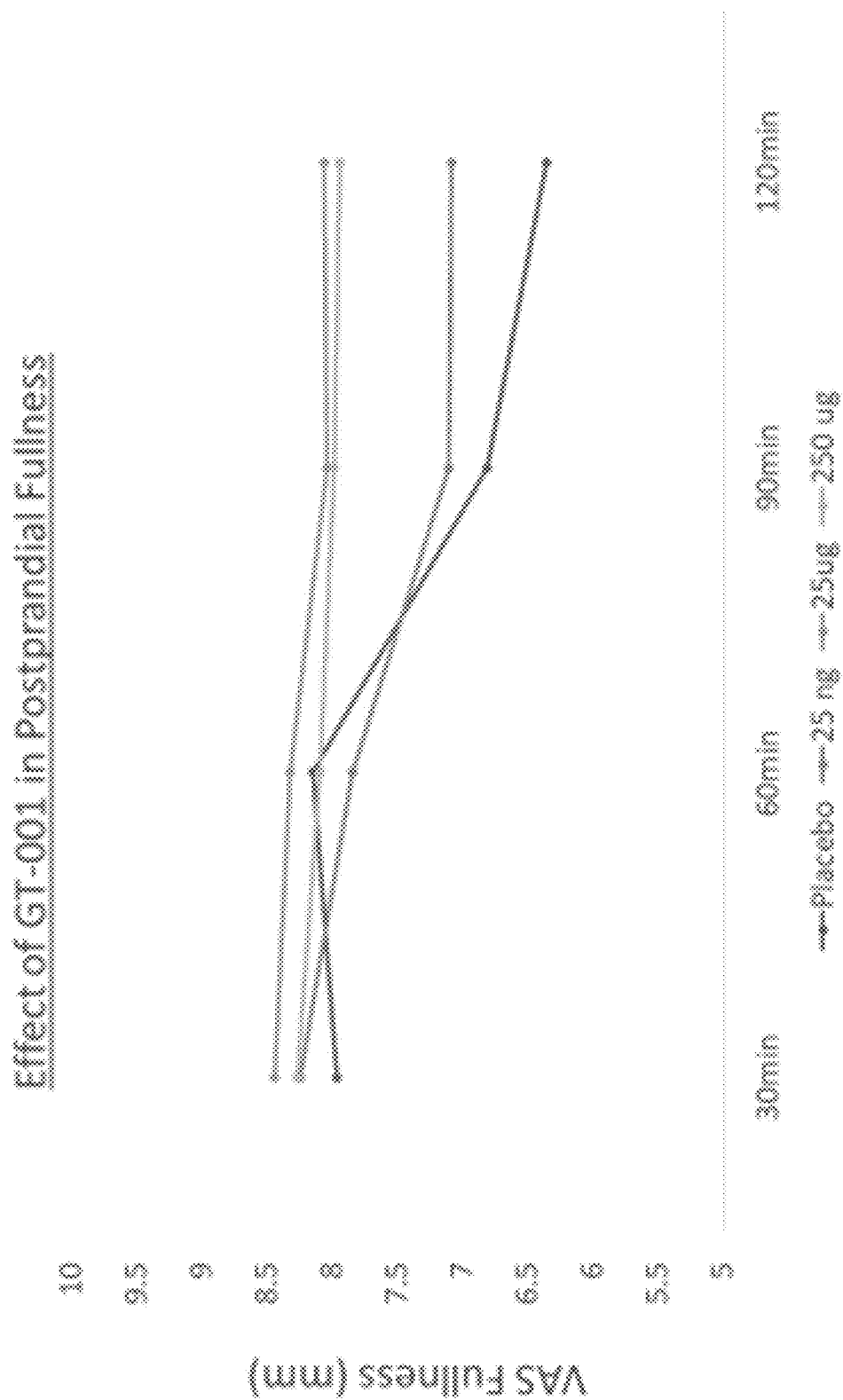
FIG. 2 shows the results of an exemplary study where the feeling of fullness (VAS Fullness (mm)) was plotted against the time post-treatment with PYY(3-36) (30 min, 60 min, 90 min, and 120 min) with a PYY(3-36) formulation, and after the subjects ate lunch at four doses (placebo, 25 ng, 25 µg, and 250 µg)

FIG. 2 shows the results of an exemplary study where the feeling of fullness (VAS Fullness (mm)) was plotted against the time post-treatment (30 min, 60 min, 90 min, and 120 min) with PYY(3-36) and after the subject ate lunch at four doses (placebo, 25 ng, 25 µg, and 250 µg). As shown in FIG. 2, doses at 25 µg and 250 µg maintain a VAS score of 8 out to 120 minutes post-lunch. A dose of 25 ng results in a VAS score of about 8 up to 60 minutes post-lunch.

Figure 3:
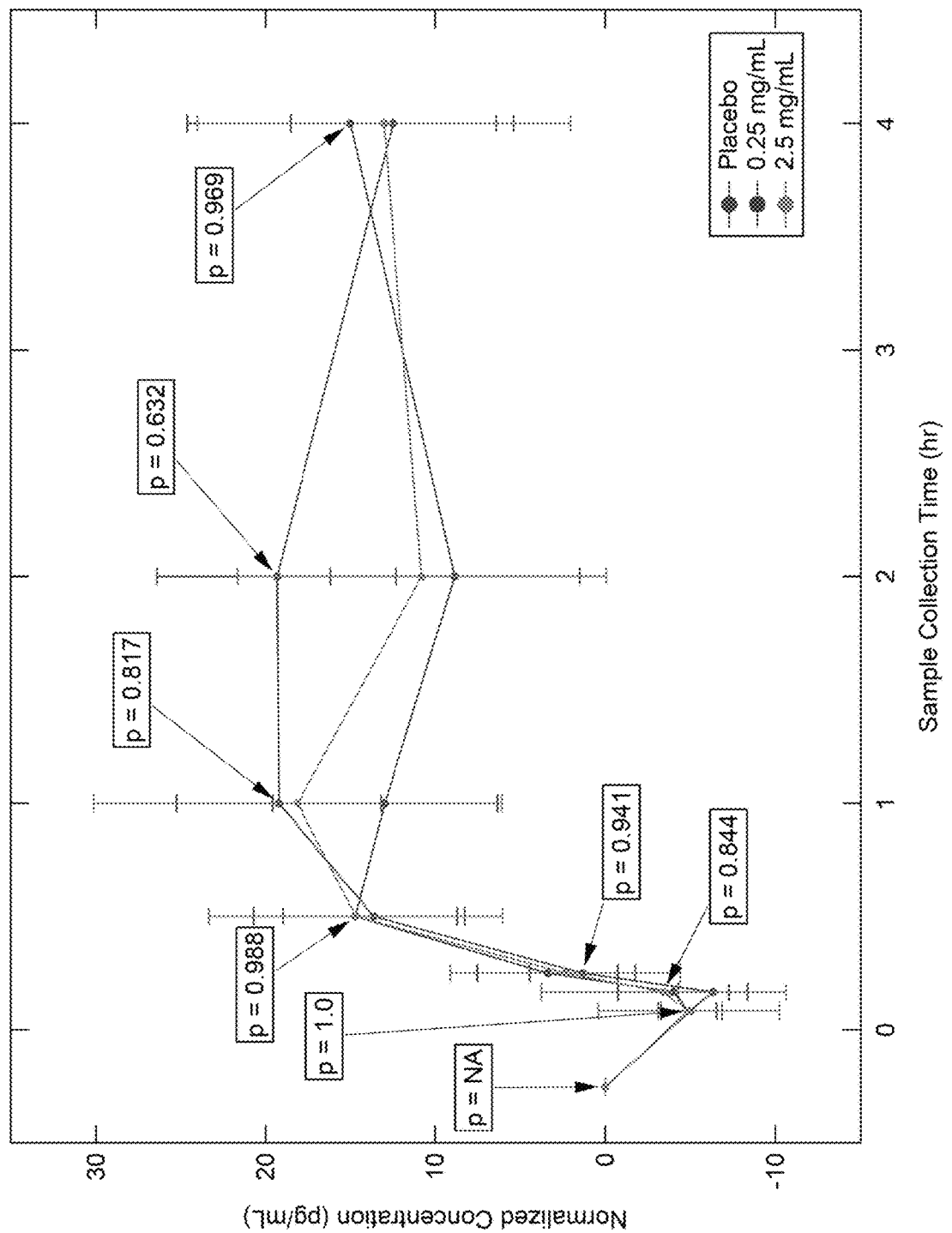
FIG. 3 shows the normalized concentration in pg/ml of PYY in the plasma of subjects receiving placebo, 0.25 mg/ml PYY(3-36), and 2.5 mg/ml PYY(3-36) formulations (each followed by lunch) measured in a time range of up to 4 hours after administration.

FIG. 3 shows the normalized concentration in pg/ml of PYY in the plasma of subjects receiving placebo, 0.25 mg/ml PYY(3-36), and 2.5 mg/ml PYY(3-36) (each followed by lunch) measured in a time range of up to 4 hours after administration. As shown, administering the placebo followed by food consumption induces the known and expected endogenous production of PYY resulting from food consumption peaking at approximately 20 pg/ml above pre-dose levels at 1-2 hours post-administration. Administering exogenous PYY(3-36) to subjects does not raise the level of PYY in plasma above levels induced by the placebo/meal combination.

Further aspects provide additional exemplary PYY(3-36) dosage forms and formulations, including, but not limited to, the following:

TABLE 3

Oral Film Strip

| Component and Quality Standard | Function | Quantity per unit (mg) | % |
|---|---|---|---|
| PYY$_{3-36}$, human | Drug substance | 2.5 ng to 2.5 mg | 5 × 10$^{-7}$ to 0.5 |
| Carboxmethylcellulose | Polymer | 225 | 45 |
| Polyethylene glycol | Plasticizer | 100 | 20 |
| Eugradit RL-100 | Polymer | 94.5 | 18.9 |
| Polysorbate 20 | Surfactant | 25 | 5 |
| Aspartame | Sweetening agent | 15 | 3 |
| Citric acid | Saliva stimulating agent, preservative | 15 | 3 |
| FD&C Blue No. 2 Aluminum Lake | Color | 0.5 | 0.1 |
| Peppermint | Flavor | 10 | 2 |
| Ethanol | Solvent | — | — |
| Purified Water | Solvent | — | — |
| Total | | 500 | 100 |

Solvents are removed during manufacture.

Further aspects provide exemplary oral film strip dosage forms as shown in Table 3. In one aspect, oral film strip pharmaceutical compositions comprising about 2.5 ng-2.5 mg of PYY(3-36) are provided. In this aspect, the oral film strip pharmaceutical composition can comprise about 2.5 ng, 25 ng, 250 ng, and 2.5 µg of PYY(3-36). In another aspect, the oral film strip pharmaceutical composition further comprises a suitable polymer, plasticizer, sweetening agent, saliva stimulating agent, preservative, and optional coloring, flavorings, and solvents. See e.g., Bala, et. al., Orally dissolving strips: A new approach to oral drug delivery system, Int J Pharm Investig. 2013 April-June; 3(2): 67-76; Tomar, Formulation and Evaluation of Fast Dissolving Oral Film of Dicyclomine as potential route of Buccal Delivery, International Journal of Drug Development & Research April-June 2012 Vol. 4 Issue 2 ISSN 0975-9344.

TABLE 4

Troche

| Component and Quality Standard | Function | Quantity per unit (mg) | % |
|---|---|---|---|
| PYY$_{3-36}$, human | Drug substance | 2.5 ng to 2.5 mg | 2.0 × 10$^{-7}$ to 0.2 |
| Polyethylene glycol | Vehicle or Base | 963.8 | 79 |
| Acacia | Suspending agent | 183 | 15 |
| Stevia | Sweetener | 36.6 | 3 |
| Peppermint | Flavor | 24.4 | 2 |
| Total | | 1220 | 100 |

Further aspects provide exemplary troche dosage forms as shown in Table 4. In one aspect, troche pharmaceutical compositions comprising about 2.5 ng-2.5 mg of PYY(3-36) are provided. In this aspect, the troche pharmaceutical composition can comprise about 2.5 ng, 25 ng, 250 ng, and 2.5 µg of PYY(3-36). In one aspect, the troche dosage form comprises PYY(3-36), a vehicle or base, and a suspending agent.

In these aspects, the suspending agent, sweetener, and flavoring components are optional. In another aspect, the vehicle or base of the troche can be sugar, made adhesive by admixture with acacia or tragacanth, fruit paste (e.g., made from black or red currants), confection of rose, or balsam of tolu. See, e.g., Kamini et al., Formulation and Percentage Evaluation of Gum-Acacia as A Binder W. S. R. to Jwaraghani Gutika (Herbo-Mineral Preparation, Int J Res Med. 2016; 5(1); 21-24 (2016).

TABLE 5

Lollipop

| Component and Quality Standard | Function | Quantity per unit (mg/mL) | Strength (label claim) % |
|---|---|---|---|
| $PYY_{3-36}$, human | Drug substance | 2.5 ng to 2.5 mg | $1.25 \times 10^{-7}$ to 0.125 |
| EMDEX (hydrated dextrose (dextrose monohydrate) containing about 7% maltodetrin | Filler, Sweetener | 1640 | 82 |
| Disodium hydrogen phosphate | Buffer | 16 | 0.8 |
| Citric acid | Preservative | 10 | 0.5 |
| Raspberry | Flavor | 4 | 0.2 |
| Confectionary sugar | Filler, Sweetener | 310 | 15.5 |
| Magnesium stearate | Lubricant | 20 | 1 |
| Total | | 2000 mg | 100 |

Further aspects provide exemplary lollipop dosage forms as shown in Table 5. In one aspect, lollipop pharmaceutical compositions can comprise about 2.5 ng-2.5 mg of PYY(3-36) are provided. In this aspect, the lollipop pharmaceutical composition comprises about 2.5 ng, 25 ng, 250 ng, and 2.5 µg of PYY(3-36). In one aspect, the lollipop dosage form comprises PYY(3-36), a filler, buffer, lubricant and a preservative. Flavoring, sweetener, are optional components. In another aspect, the lollipop dosage form further comprises maltose-dextrose, water, and cornstarch or another binding material. In another aspect, the lollipop dosage form further comprises maltose-dextrose, water, and cornstarch or another binding material. See, e.g., US Patent Application Publication 2007/0104763.

TABLE 6

Chewing Gum

| Component and Quality Standard | Function | Quantity per unit (mg/mL) | Strength (label claim) % |
|---|---|---|---|
| $PYY_{3-36}$, human | Drug substance | 2.5 ng to 2.5 mg | $2.5 \times 10^{-7}$ to 0.25 |
| Compressible Gum Base Powder (e.g., Health in Gum ®) | Gum base | 883 | 88.3 |
| Sorbitol | Granulating agent, Sweetener | 100 | 10 |
| Magnesium stearate | Lubricant | 10 | 1 |
| Citric acid | Preservative, salivating agent | 5 | 0.5 |
| Peppermint | Flavor | 2 | 0.2 |
| Total | | 1000 mg | 100 |

Further aspects provide exemplary chewing gum dosage forms as shown in Table 6. In one aspect, chewing gum pharmaceutical compositions comprising about 2.5 ng-2.5 mg of PYY(3-36) are provided. In this aspect, the chewing gum pharmaceutical composition can comprise about 2.5 ng, 25 ng, 250 ng, and 2.5 µg of PYY(3-36). In one aspect, the chewing gum dosage form comprises PYY(3-36), a gum base, a granulating agent, a lubricant, a preservative, and a lubricant. Flavoring, and sweeteners are optional components. See, e.g., Aslani, et al., Medicated chewing gum, a novel drug delivery system, J. Res Med Sci. 2015 April; 20(4): 403-411. Alternatively, chewing gum dosage forms can be made by direct compression. See, e.g., U.S. Pat. No. 7,208,186. See, also, Heema et. al., Medicated chewing gums-updated review. Int J Pharm Res Dev. 2010; 2:66-76.

Further aspects provide spray-dried particle dosage forms (e.g., sachet of spray-dried particles) as shown in Tables 7-9. In these aspects, pharmaceutical compositions comprising about 2.5 ng-2.5 mg of PYY(3-36) are provided. The exemplary spray-dried pharmaceutical composition comprises about 2.5 ng, 25 ng, 250 ng, and 2.5 µg of PYY(3-36).

TABLE 7

Spray-Dried Particles, Example 1

| Component and Quality Standard | Function | Quantity per unit (mg/mL) | Strength (label claim) % |
|---|---|---|---|
| $PYY_{3-36}$, human | Drug substance | 2.5 ng to 2.5 mg | $2.5 \times 10^{-7}$ to 0.25 |
| Anhydrous α Lactose | Carrier | 800 | 80 |
| Sorbitol | Granulating agent, Sweetener | 93 | 9.3 |
| Disodium Hydrogen Phosphate | Buffer | 100 | 10 |
| Potassium Sorbate, NF | Preservative | 5 | 0.5 |
| Flavor | Flavor | 2 | 0.2 |
| Purified Water | Solvent/suspending solution | — | — |
| Total | | 1000 mg | 100 |

Solvent is removed during manufacture.

In the aspect of Table 7, a drug (e.g., PYY(3-36) can be mixed with excipients into a solution or suspension, and sprayed to form a particle. For example, PYY(3-36) and the excipients of Table 7 can be combined with lactose in solution or suspension and spray-dried followed by collection of particles on a filter. See, e.g., Luhn, *Using Excipients In Powder Formulations*, Pharmaceutical Technology Europe, Vol. 23, Issue 1 (Jan. 7, 2011); Wu et al., *Studies on the spray dried lactose as carrier for dry powder inhalation*, Asian Journal of Pharmaceutical Sciences 9 (2014) 336-341.

TABLE 8

Spray-Dried Particles - Example 2

| Component and Quality Standard | Function | Quantity per unit (mg/mL) | % |
|---|---|---|---|
| | | | Strength (label claim) |
| $PYY_{3-36}$, human | Drug substance | 2.5 ng to 2.5 mg | $2.5 \times 10^{-7}$ to 0.25 |
| Spray-dried Lactose Monohydrate | Filler | 800 | 80 |
| Sorbitol | Granulating agent, Sweetener | 93 | 9.3 |
| Disodium Hydrogen Phosphate | Buffer | 100 | 10 |
| Potassium Sorbate, NF | Preservative | 5 | 0.5 |
| Flavor | Flavor | 2 | 0.2 |
| Purified Water | Solvent/suspending solution | — | — |
| Total | | 1000 mg | 100 |

Solvent is removed during manufacture.

In the aspect of Table 8, the drug and excipients can be wet granulated with commercially available spray dried lactose and then dried. See, e.g., Huang et al., *Using spray-dried lactose monohydrate in wet granulation method for a low-dose oral formulation of a paliperidone derivative*, Powder Technology 246 (2013) 379-394. In one aspect, the dosage form can be a filled sachet of spray dried particles.

TABLE 9

Spray-Dried Particles - Example 3

| Component and Quality Standard | Function | Quantity per unit (mg/mL) | % |
|---|---|---|---|
| | | | Strength (label claim) |
| $PYY_{3-36}$, human | Drug substance | 2.5 ng to 2.5 mg | $2.5 \times 10^{-7}$ to 0.25 |
| Anhydrous α Lactose | Carrier | 800 | 80 |
| Sorbitol | Granulating agent, Sweetener | 93 | 9.3 |
| Disodium Hydrogen Phosphate | Buffer | 100 | 10 |
| Potassium Sorbate, NF | Preservative | 5 | 0.5 |
| Flavor | Flavor | 2 | 0.2 |
| Purified Water | Solvent/suspending solution | — | — |
| Total | | 1000 mg | 100 |

Solvent is removed during manufacture.

In the aspect of Table 9, the drug and excipients can be sprayed onto commercially available lactose or pre-step spray dried lactose, as described. Asian Journal of Pharmaceutical Sciences 9 (2014) 336-341.

In another aspect, the spray-dried particles from, for example, Tables 7-9, can be delivered in dry powder inhaler (propellant). In one aspect, the size of the spray-dried particles is between 1 to 10 microns to avoid blocking the orifice of the inhaler device, yet, for example, large enough to be less likely to be inhaled and to be mostly deposited in the mouth. In this aspect, the propellant can be HFA 134a or HFA 227, or a combination of the two. The nozzle design on the inhaler could be adapted to facilitate actuation of a dose to the tongue. In yet another aspect, spray-dried particles could be delivered without propellant (e.g., using a unit dose delivery device such as the Aptar pharma UDS device).

Further aspects provide microporous polysaccharide microsphere dosage forms.

TABLE 10

Frozen Particles

| Component and Quality Standard | Function | Quantity per unit (mg/mL) | % |
|---|---|---|---|
| | | | Strength (label claim) |
| $PYY_{3-36}$, human | Drug substance | 2.5 ng to 2.5 mg | $2.5 \times 10^{-7}$ to 0.25 |
| Spray-dried Lactose Monohydrate | Filler | 800 | 80 |
| Sorbitol | Granulating agent, Sweetener | 93 | 9.3 |
| Disodium Hydrogen Phosphate | Buffer | 100 | 10 |
| Potassium Sorbate, NF | Preservative | 5 | 0.5 |
| Flavor | Flavor | 2 | 0.2 |
| Purified Water | Solvent/suspending solution | QS to 1000 mL | QS to 100 |
| Total | | 1000 mg | 100 |

Further aspects provide exemplary frozen particle dosage forms as shown in Table 10. In one aspect, frozen particle pharmaceutical compositions comprising about 2.5 ng-2.5 mg of PYY(3-36) are provided. In this aspect, the frozen particle pharmaceutical composition can comprise about 2.5 ng, 25 ng, 250 ng, and 2.5 µg of PYY(3-36). In this aspect, the pharmaceutical compositions comprise PYY(3-36), a filler, a granulating agent, a buffer, a preservative, and a solvent/suspending agent. Optional sweeteners and flavorings can be added. In this aspect, the wet granulation method described above with respect to Table 8 can be used. However, instead of a drying step, the particles can be filled into sachets of frozen particles and frozen.

Alternatively, a frozen PYY(3-36) solution (Table 11, below) can be used to fill tubes prior to freezing. Any suitable tube can be used (e.g., polypropylene tubes used generally for pharmaceuticals, cosmetics, and food). The tube can be flexible to permit the frozen solution to be dispensed on to the tongue and thawed slowly, for example. In yet another aspect, the frozen solution can be used in a "blow, fill, seal" dosage form and dispensed in a manner similar to an eye drop or mouthwash dispenser. Markarian, "Blow-fill-seal Technology Advances in Aseptic Filling Applications: New advanced aseptic manufacturing technologies are available for filling liquid pharmaceuticals, including biologics, Equipment and Processing Report, Jun. 18, 2014.

TABLE 11

Frozen Solution

| Component and Quality Standard | Function | Quantity per unit (mg/mL) | Strength (label claim) % |
|---|---|---|---|
| $PYY_{3-36}$, human | Drug substance | 2.5 ng to 2.5 mg | $2.5 \times 10^{-7}$ to 0.25 |
| Sorbitol | Granulating agent, Sweetener | 100 | 10 |
| Disodium Hydrogen Phosphate | Buffer | 100 | 10 |
| Potassium Sorbate, NF | Preservative | 5 | 0.5 |
| Flavor | Flavor | 2 | 0.2 |
| Polyethylene Glycol 8000 | Stabilizer | 100 | 10 |
| Purified Water | Solvent/suspending solution | QS to 1 mL | QS to 100 |

TABLE 12

Lyophilized Particles

| Component and Quality Standard | Function | Quantity per unit (mg) | Strength (label claim) % |
|---|---|---|---|
| $PYY_{3-36}$, human | Drug substance | 2.5 ng to 2.5 mg | $5.0 \times 10^{-6}$ to 5.0 |
| Trehalose | Cryoprotectant/Stabilizer | 25.5 to 28 | 51 to 56 |
| Edetate Disodium, Dihydrate, USP | Antioxidant | 1 | 2.0 |
| Sodium Phosphate, Monobasic, Dihydrate, USP | Buffer | 3 | 6.0 |
| Potassium Sorbate, NF | Preservative | 2 | 0.20 |
| Hydrochloric Acid (HCl), NF, USP | pH modifier | QS to pH 7.0 ± 0.1 | — |
| Sodium Hydroxide (NaOH), USP | pH modifier | QS to pH 7.0 ± 0.1 | — |
| Purified Water | Solvent | — | — |

Solvent is removed during manufacture. Diluent can be sterile water or dextrose 5%.

Further aspects provide exemplary lyophilized particle dosage forms as shown in Table 12. In one aspect, lyophilized particle pharmaceutical compositions comprising about 2.5 ng-2.5 mg of PYY(3-36) are provided. In this aspect, the lyophilized particle pharmaceutical composition can comprise about 2.5 ng, 25 ng, 250 ng, and 2.5 µg of PYY(3-36). In this aspect, the pharmaceutical compositions comprise PYY(3-36), a cryoprotectant/stabilizer, an antioxidant, a buffer, preservative(s), optional pH modifiers, and a solvent.

In one aspect, the lyophilized particles are separated from the diluent in a pre-filled oral syringe with mixing chamber. See, e.g., Vetter-Pharma, Vetter Dual Chamber Systems Website Description. In another aspect, the lyophilized particles are separated from the diluent with a mixing chamber.

TABLE 13

Oral Spray

| Component and Quality Standard | Function | Quantity per unit (mg) | Strength (label claim) % |
|---|---|---|---|
| $PYY_{3-36}$, human | Drug substance | 2.5 ng to 2.5 mg | $2.5 \times 10^{-7}$ to 0.25% |
| Aspartame | Sweetening agent | 30 | 3 |
| Edetate Disodium, Dihydrate, USP | Antioxidant | 20 | 2.0 |
| Sodium Phosphate, Monobasic, Dihydrate, USP | Buffer | 60 | 6.0 |
| Potassium Sorbate, NF | Preservative | 2 | 0.20 |
| Peppermint | Flavor | 10 | 1 |

TABLE 13-continued

Oral Spray

| Component and Quality Standard | Function | Quantity per unit (mg) | Strength (label claim) % |
|---|---|---|---|
| Hydrochloric Acid (HCl), NF, USP | pH modifier | QS to pH 7.0 ± 0.1 | — |
| Sodium Hydroxide (NaOH), USP | pH modifier | QS to pH 7.0 ± 0.1 | — |
| Purified Water | Solvent | QS to 1 mL | QS to 100 |

Further aspects provide exemplary oral spray dosage forms as shown in Table 13. In one aspect, oral spray pharmaceutical compositions comprising about 2.5 ng-2.5 mg of PYY(3-36) are provided. In this aspect, the oral spray pharmaceutical composition can comprise about 2.5 ng, 25 ng, 250 ng, and 2.5 µg of PYY(3-36). In this aspect, the pharmaceutical compositions comprise PYY(3-36), an antioxidant, a buffer, a preservative, a solvent, optional pH modifiers, and optional flavorings and sweetener agents.

In another aspect, the oral spray can be one device (CCS with activator), an oral spray with vial adaptor for actuator at the time of administration, an oral spray solution to be poured into a device with an actuator, an oral solution in a prefilled oral syringe, an oral solution in a blow-filled sealed tube, an oral solution in vial or tube with a measuring device (e.g., dropper, syringe), or a small squeeze bottle that dispenses drops (e.g., similar to an optical solution).

TABLE 14

Softgel Capsule

| Component and Quality Standard | Function | Quantity per unit (mg) | Strength (label claim) % |
|---|---|---|---|
| $PYY_{3-36}$, human | Drug substance | 2.5 ng to 2.5 mg | $2.5 \times 10^{-7}$ to 0.25% |
| Gelatin A | Shell | 440 | 44 |
| Glycerin | Base | 40 | 4 |
| Sorbitol | Sweetening Agent | 100 | 10 |
| Polyethylene Glycol 400 | Base | 30 | 3 |
| Peppermint | Flavor | 20 | 2 |
| Potassium Sorbate, NF | Preservative | 2 | 0.2 |
| Color | Color | 1.5 | 0.15 |
| Purified Water | Solvent | QS to 1 mL | QS to 100 |

Further aspects provide exemplary softgel capsule dosage forms as shown in Table 14. In one aspect, softgel capsule pharmaceutical compositions comprising about 2.5 ng-2.5 mg of PYY(3-36) are provided. In this aspect, the softgel capsule pharmaceutical composition can comprise about 2.5 ng, 25 ng, 250 ng, and 2.5 µg of PYY(3-36). In this aspect, the pharmaceutical compositions comprise PYY(3-36), a shell (e.g., gelatin), a base (e.g., glycerin), a second base (polyethylene glycol), a preservative, a solvent, optional flavorings, coloring, and sweetener agents. In another aspect, the softgel capsule can have a removable nib to open the capsule and pour the contents on to the tongue.

TABLE 15

Mouthwash

| Component and Quality Standard | Function | Quantity per unit (mg) | Strength (label claim) % |
|---|---|---|---|
| $PYY_{3-36}$, human | Drug substance | 2.5 ng to 2.5 mg | $2.5 \times 10^{-7}$ to 0.25% |
| Sucralose | Sweetening agent | 30 | 3 |
| Edetate Disodium, Dihydrate, USP | Antioxidant | 20 | 2.0 |
| Glycerin | Solvent | 80 | 8.0 |
| 95% ethanol | Solvent, preservative | 100 | 10.0 |
| Peppermint | Flavor | 200 | 20 |
| PEG-40 Sorbitan Diisostearate | Surfactant | 400 | 40.0 |
| Purified Water | Solvent | QS to 1 mL | QS to 100 |

Further aspects provide exemplary mouthwash dosage forms as shown in Table 15. In one aspect, mouthwash pharmaceutical compositions comprising about 2.5 ng-2.5 mg of PYY(3-36) are provided. In this aspect, the mouthwash pharmaceutical composition can comprise about 2.5 ng, 25 ng, 250 ng, and 2.5 µg of PYY(3-36). In this aspect, the pharmaceutical compositions comprise PYY(3-36), an antioxidant, a surfactant, a preservative, and a solvent(s). Optional flavorings and sweeteners may also be added.

TABLE 16

Buccal Tablets - Example 1

| Component and Quality Standard | Function | Quantity per unit (mg/mL) | Strength (label claim) % |
|---|---|---|---|
| $PYY_{3-36}$, human | Drug substance | 2.5 ng to 2.5 mg | to 1.7 $1.7 \times 10^{-6}$ |
| Hydroxypropyl methylcellulose (HPMC) 15 cps | Binder/Mucoadhesive | 10 | 6.7 |
| Mannitol | Sweetener/Diluent | 40 | 26.7 |
| Carbopol 934P | Mucoadhesive | 10 | 6.7 |
| Aspartame | Sweetener | 3 | 2.0 |
| Sodium stearyl fumarate (SSF) | Lubricant | 3 | 2.0 |
| Spray-dried flavor agent | Flavor | 3 | 2.0 |
| Polyvinyl pyrrolidone K30 | Dispersant/mucoadhesive | 6 | 4.0 |
| Ethyl cellulose | Filler/Binder/Viscosity Enhancer/Mucoadhesive | 72.5 to 75 | 48.3 to 50.0 |
| Total | | 150 | 100 |

Further aspects provide exemplary buccal tablet dosage forms as shown in Table 16. In one aspect, buccal tablet pharmaceutical compositions comprising about 2.5 ng-2.5 mg of PYY(3-36) are provided. In this aspect, the buccal tablet pharmaceutical composition can comprise about 2.5 ng, 25 ng, 250 ng, and 2.5 µg of PYY(3-36). In this aspect, the pharmaceutical compositions comprise PYY(3-36), mucoadhesive(s), a dispersant, a preservative, a lubricant, and fillers or binders. Optional flavorings and sweeteners may also be added. See, e.g., Shirsand et. al., *Formulation and optimization of mucoadhesive bilayer buccal tablets of atenolol using simplex design method*, Int J Pharm Investig. 2012 January-March; 2(1): 34-41.

TABLE 17

Buccal Tablets - Example 2

| Component and Quality Standard | Function | Quantity per unit (mg) | Strength (label claim) % |
|---|---|---|---|
| $PYY_{3-36}$, human | Drug substance | 2.5 ng to 2.5 mg | $2.1 \times 10^{-6}$ to 2.1 |
| Hydroxypropyl methylcellulose K4M | Binder/Mucoadhesive | 30 | 25 |
| Carbopol 934P | Mucoadhesive | 5 | 4.2 |
| Xantham gum | Mucoadhesive | 30 | 25 |
| Lactose | Diluent/Filler/Binder | 51.3 to 53.8 | 42.8 to 44.8 |
| Magnesium Stearate | Lubricant | 1.2 | 1.0 |
| Total | | 120 | 100 |

Further aspects provide exemplary buccal tablet dosage forms as shown in Table 17. In one aspect, buccal tablet pharmaceutical compositions comprising about 2.5 ng-2.5 mg of PYY(3-36) are provided. In this aspect, the buccal tablet pharmaceutical composition can comprise about 2.5 ng, 25 ng, 250 ng, and 2.5 µg of PYY(3-36). In this aspect, the pharmaceutical compositions comprise PYY(3-36), mucoadhesive(s), a lubricant, and diluents, fillers or binders. See, e.g., Chaudhari et al., *Formulation and Evaluation of Buccal Tablet of Salbutamol Sulphate*, IRJP 2011, 2 (12), 238-242.

TABLE 18

Lyophilized Tablet

| Component and Quality Standard | Function | Quantity per unit (mg) | Strength (label claim) % |
|---|---|---|---|
| $PYY_{3-36}$, human | Drug substance | 2.5 ng to 2.5 mg | $5.0 \times 10^{-6}$ to 5.0 |
| Polyvinyl pyrrolidone | Mucoadhesive | 2.5 | 5.0 |
| Carbopol 934P | Mucoadhesive | 5 | 10 |
| Trehalose | Cryoprotectant/Stabilizer | 25.5 to 28 | 51 to 56 |
| Edetate Disodium, Dihydrate, USP | Antioxidant | 1 | 2.0 |
| Sodium Phosphate, Monobasic, Dihydrate, USP | Buffer | 3 | 6.0 |
| Polysorbate 20, NF | Surfactant | 3 | 6.0 |
| Hydrochloric Acid (HCl), NF, USP | pH modifier | QS to pH 7.0 ± 0.1 | — |
| Sodium Hydroxide (NaOH), USP | pH modifier | QS to pH 7.0 ± 0.1 | — |
| Sterile Water for Injection, USP | Solvent | — | — |

Solvent removed during manufacturing

Further aspects provide exemplary lyophilized tablet dosage forms as shown in Table 18. In one aspect, lyophilized tablet pharmaceutical compositions comprising about 2.5 ng-2.5 mg of PYY(3-36) are provided. In this aspect, the lyophilized tablet pharmaceutical composition can comprise about 2.5 ng, 25 ng, 250 ng, and 2.5 µg of PYY(3-36). In this aspect, the pharmaceutical compositions comprise PYY(3-36), mucoadhesive(s), a surfactant, a cryoprotectant/stabilizer, an antioxidant, and pH modifiers and solvent.

TABLE 19

Oral Dissolving Tablet ("ODT")

| Component and Quality Standard | Function | Quantity per unit (mg) | Strength (label claim) % |
|---|---|---|---|
| $PYY_{3-36}$, human | Drug substance | 2.5 ng to 2.5 mg | $5 \times 10^{-7}$ to 1.0 |
| Microcrystaline cellulose | Binder | 100 | 40 |
| Mannitol | Binder | 119.75 | 45.9 |
| Crospovidone | Disintegrant | 25 | 10 |
| Aspartame | Sweetening agent | 5 | 2 |
| FD&C Blue No. 2 Aluminum Lake | Color | 0.25 | 0.1 |
| Peppermint | Flavor | 1.25 | 0.5 |
| Magnesium stearate | Lubricant | 1.25 | 0.5 |
| Total | | 250 | 100 |

Further aspects provide exemplary ODT tablet dosage forms as shown in Table 19. In one aspect, ODT tablet pharmaceutical compositions comprising about 2.5 ng-2.5 mg of PYY(3-36) are provided. In this aspect, the ODT tablet pharmaceutical composition can comprise about 2.5 ng, 25 ng, 250 ng, and 2.5 µg of PYY(3-36). In this aspect, the pharmaceutical compositions comprise PYY(3-36), binder(s), a disintegrant, a lubricant, and optional sweetening agents, flavorings, and lubricants.

In one aspect, the ODT tablet dosage form is a blended powder system that is subsequently compressed into tablets using standard rotary press, and packaged into blister packs or bottles depending on the friability of the tablets. Finished tablets can have a disintegration time of 30 seconds or less on the tongue, for example. Flavoring, coloring, and sweetener levels can be varied as required for end-user experience.

The compositions described herein can be used to treat a patient in need of treatment as described herein. The terms "treat," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial. The terms "treatment" or "prevention" also refer to delaying onset of a disease for a period of time or delaying onset indefinitely. The term "treatment" or "treating" refers to administering a drug or treatment to a patient or prescribing a drug to a patient where the patient or a third party (e.g., caretaker, family member, or health care professional) administers the drug or treatment.

The components of the compositions described herein also encompass derivatives and analogs. In one embodiment, the terms "derivative" or "analogs" include, but are not limited to, ether derivatives, acid derivatives, amide derivatives, ester derivatives and the like. Methods of preparing these derivatives are known to a person skilled in the art. For example, ether derivatives are prepared by the coupling of the corresponding alcohols. Amide and ester derivatives are prepared from the corresponding carboxylic acid by a reaction with amines and alcohols, respectively.

Any suitable dosage form can be used for delivery of the pharmaceutical compositions described herein in addition to dosage forms and formulations described above. In one aspect, the dosage form is especially suitable for intraoral or oromucosal delivery. In another aspect, the dosage form is a lozenge (e.g., planar sheet, solid or semi-solid candy). In another aspect, the dosage form is a gel, cream, foam, orally disintegrating tablets, or paste. The lozenge can comprise dissolvable material. In another aspect, the dosage form comprises chewing gum. In yet another aspect, the dosage form is a liquid formulation (e.g., emulsion, syrup, elixir, suspension, or a solution, gargles, mouthwashes, gingival solutions, oromucosal solutions and oromucosal suspensions, semi-solid oromucosal preparations (including for example gingival gel, gingival paste, oromucosal gel, oromucosal paste), oromucosal drops, oromucosal sprays and sublingual sprays (including oropharyngeal sprays), lozenges and pastilles, compressed lozenges, sublingual tablets and buccal tablets, oromucosal capsules, mucoadhesive preparations.). In a further aspect, the liquid formulation is a spray or drops for oral administration.

In one aspect, compositions described herein, or a thereof can be compounded or used as a starting material for compounding with a physiologically acceptable vehicle, carrier, excipient, binder, preservative, stabilizer, flavor, etc., in a unit dosage form as called for by accepted pharmaceutical practice. The amount of active substance in compositions or preparations (e.g., active pharmaceutical ingredients) comprising the components of compositions described herein is such that a suitable dosage in the range indicated is obtained, as described herein.

In another aspect, the components of compositions described herein can be formulated in a unit dosage form. The term "unit dosage from" refers to physically discrete units suitable as unitary dosages for human subjects and other mammals, each unit containing a predetermined quantity of active material calculated to produce the desired therapeutic effect, in association with one or more suitable pharmaceutical excipients.

In one aspect, one or more of the components of compositions described herein are mixed with or used as starting materials mixed with a suitable pharmaceutically acceptable carrier to form compositions, for example, as described herein. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of the components of compositions described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if the components of compositions described herein exhibit insufficient solubility, methods for solubilizing may be used. Such methods are known and include, but are not limited to, using co-solvents such as dimethylsulfoxide (DMSO), using surfactants such as TWEEN® (e.g., polysorbate), and dissolution in aqueous sodium bicarbonate.

The concentration of the compound is effective for delivery of an amount upon administration that lessens or ameliorates at least one symptom of the disorder for which the compound is administered. Typically, the compositions are packaged for unit dosage administration.

In another aspect, the components of compositions described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, the components of compositions described herein can be enclosed in multiple or single dose containers. The enclosed compounds and compositions can be provided in kits, for example, including component parts that can be assembled for use. For example, one or more of the compounds (e.g., PYY, PYY(3-36), or analogs) can be used as a starting material for a lyophilized form (e.g., lyophilized oral dissolving tablet) and a suitable diluent may be provided as a separated component for combination prior to use. A kit may include components of compositions described herein and a second or third therapeutic agent for co-administration. The components of compositions described herein and the second or third therapeutic agent may be provided as separate component parts. A kit may include a plurality of containers, each container holding one or more unit dose of the components of compositions described herein. In one aspect, the containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

In yet another aspect, the dosage form is lyophilized oral dissolving tablets. The lyophilized oral dissolving tablets can be modified with the addition of sugars to produce, for example, a higher Tg Add in lyophilized oral dissolving tablets these can include sugars that produce Tg (glass transition temperature) higher than room temperature. See, e.g., Elnggar et al., Maltodextrin: A Novel Excipient Used in Sugar-Based Orally Disintegrating Tablets and Phase Transition Process, AAPS PharmSciTech. 2010 June; 11(2): 645-651 (Apr. 20, 2010).

The concentration of the components of compositions described herein will depend on dissolution, absorption, metabolism, and excretion rates of the active compound(s), the dosage schedule, and amount administered as well as other factors known to those of skill in the art.

In another aspect, the active ingredients may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be optionally lyophilized and compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. The components of compositions described herein can be used, for example, in combination with an anti-obesity, anti-diabetes, or similar drug (e.g., lorcaserin, orlistat, phentermine/topiramate, sibutramine, rimonabant, metformin, exenatide, liraglutide, pamlintide, naltrexone, and tesofensine).

In one aspect, solutions or suspensions used for parenteral, pump delivery, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA) or its disodium salt; buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropylene glycol, and mixtures thereof. Liposomal suspensions including tissue-targeted liposomes may also be suitable as pharmaceutically acceptable carriers. These may be prepared according to methods known in the art.

In another aspect, the components of compositions described herein may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, hydroxyl propyl methyl cellulose (HPMC), other cellulose derivatives, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The oral dosage forms can be administered to the patient 1, 2, 3, or 4 times daily, or as needed. The components of compositions described herein can be administered either three or fewer times, or even once or twice daily. Whatever oral dosage form is used, it can be designed so as to protect the compounds employed in the methods described herein from the acidic environment of the stomach. Enteric coated tablets and capsules filled with small spheres, each coated to protect from the acidic stomach, are also well known to those skilled in the art and can be used with aspects described herein.

The terms "therapeutically effective amount" and "therapeutically effective period of time" are used to denote treatments at dosages and for periods of time effective to treat, ameliorate, or reduce conditions or symptoms described herein.

One of skill in the art will appreciate that such therapeutic effect resulting in a lower effective concentration of the components of compositions described herein may vary considerably depending on the tissue, organ, or the particular animal or patient to be treated. It is also understood that while a patient may be started at one dose, that dose may be varied overtime as the patient's condition changes.

It should be apparent to one skilled in the art that the exact dosage and frequency of administration will depend on the particular compounds employed in the methods of the disclosure administered, the particular condition being treated, the severity of the condition being treated, the age, weight, general physical condition of the particular patient, and other medication the individual may be taking as is well known to administering physicians who are skilled in this art.

EXAMPLES

Example 1—PYY(3-36) Dose Escalation Study

Day 1 (Check into Study Unit and Placebo Administration)

Subjects who complete all screening procedures and meet all inclusion and exclusion criteria described within the protocol and found to be eligible for study enrollment checked into the Study Unit (i.e., the study facility). The morning of the study, participants fasted prior to arriving at the SU. Participants fasted for at least 12 hours prior to Day 1 of the study. Participants were permitted to only drink water prior to arrival to SU and were able to brush their teeth. The following assessments and measurements were taken:

(1) Inspection of the lingual mucosa.
(2) Updating medical and medication history prior to placebo application.
(3) Assessing health status. If participant has either rhinitis or gastrointestinal distress, the participant will be discontinued for that day.
(4) Measuring body weight and BMI.
(5) Measuring vital signs (BP, HR, and body temperature). BP and HR were measured twice in the sitting position and twice in the standing position. If BP was high at baseline sitting (>160 systolic), BP was re-checked after participant was sitting for 5-10 min. Body temperature was measured once.
(6) Performing urine drug screen, urine cotinine test, alcohol breath test, and urine pregnancy test.
(7) Subjects provided a 325-400 calorie breakfast and calorie intake was recorded.
(8) Water was provided "ad-libitum" and volume recorded.
(9) Four (4) hours post breakfast, the VAS for Appetite and Satiety was performed.
(10) Inserting a cannula to obtain blood samples, obtaining a 5 ml blood sample, and screening for anti-GT-001 antibodies.
(11) Obtaining a fasting PK blood sample #1 (5 ml) 15 minutes prior to placebo.
(12) Performing a water mouthwash prior to dosing with GT-001. The mouthwash can be a rinse with 20 ml of water.
(13) Giving one milliliter (1 ml) of placebo (formulation without GT-001) to the participant to the tongue via pipette 5 minutes before lunch.
(14) The solution remained on the tongue for 1 minute followed by asking participants to swish and then swallow.
(15) Completing a VAS for like-lines (VAS completed by subjects).
(16) Collecting PK blood samples after each of seven doses at ±1 minute at 5, 10, 15, 30, and ±5 minutes at 60, 120, and 240 minutes post dose.
(17) Isolating subjects from other subjects during lunch.
(18) Provided a "ad-libitum" lunch (composed of a casserole, nutrient drink and two (2) cookies) and recording calorie intake.
(19) Having subjects complete VAS questionnaire for sweetness, sourness, bitterness, saltiness, umami, and fat taste 20 minutes after completing the meals.
(20) Recording VAS for appetite and satiety every 30 minutes for 2 hours after completing the meal.
(21) Discharging subjects. Subjects ate "at-libitum" until the 12-hour fasting period preceding the next study visit.
(22) During the SU visit, subjects were restricted from ingesting gum, candy, tobacco, carbonated drinks, and from performing exercise. During the meal, subjects were not exposed to food cues (visual, odor, or hearing) and they should eat in isolation.

Days 2, 4, 6, 8, 10, 12 and 14 treatment days are the same as day 1.

Days 3, 5, 7, 9, 11, and 13: Washout days
Participants rest at home.
Study End (Day 15 and Early Termination Visit
If an enrolled subject completed day 1-14, or discontinued from the study prior to the planned SU discharge, the following was completed:

(1) Recording reason for discontinuation from the study.
(2) Updating medical and medication history.
(3) Completing adverse event assessment.
(4) Measuring vital signs (BP, HR, and body temperature). BP and HR were measured twice in the sitting position and twice in the standing position. If BP is high at baseline sitting (>160 systolic), BP was re-checked after participant is sitting for 5-10 minutes. Body temperature was measured once.
(5) Measuring body weight and BMI.
(6) Performing physical examination, including inspection of the lingual mucosa.
(7) Conducting clinical laboratory tests (serum chemistry, hematology, and urinalysis).
(8) Measuring GT-001 serum level with anti-GT-001 antibodies.
(9) Giving serum pregnancy test.
(10) Performing urine drug screen, urine cotinine test, and alcohol breath test.
(11) Diet: Meals details
(a) Breakfast: Participants provided with macronutrient balanced breakfast (approximately 325-400 calories). Participants selected their type of breakfast between eggs, cereal, toast, etc. Juices, milk and coffee were permitted within the allotted calories. No artificial sweeteners were permitted.
(b) Lunch: Participants provided with all you can eat casserole, juice/milk, and two (2) cookies. Total food intake and VAS appetite and satiety was recorded. No artificial sweeteners were permitted.

(c) In between meals: Participants can only have water in between meals. Participants were restricted from gum, candy, tobacco, and carbonated drinks.

Example 2—VAS Assessment

The following exemplary VAS Assessment was given to subjects to assess their feeling of fullness before and after receiving PYY(3-36) or placebo and before or after eating at various doses described herein. Participants indicated their response on a scale of 1-10 with 1 indicating the strongest response on the left and 10 indicating the strongest response on the right. For example, if a participant indicated a response of 1 for question a, they were not hungry at all. A response of 10 for question a indicated they have never been hungrier. A response of 5 indicates they felt in between "I am not hungry at all" and "I have never been more hungry." The numerical responses on a scale of 1-10 were tabulated and used to generate the graphs of FIGS. 1 and 2.

| a | I am not hungry at all | How hungry do you feel? | I have never been more hungry |
|---|---|---|---|
| b | I am completely empty | How satisfied do you feel? | I cannot eat another bite |
| c | Not at all full | How full do you feel? | Totally full |
| d | Nothing at all | How much do you think you can eat? | A lot |

REFERENCES

1. Ng M, Fleming T, Robinson M, et al. Global, regional, and national prevalence of overweight and obesity in children and adults during 1980-2013: a systematic analysis for the Global Burden of Disease Study 2013. Lancet 2014
2. Acosta A, Abu Dayyeh B K, Port J D, Camilleri M. Recent advances in clinical practice challenges and opportunities in the management of obesity. Gut 2014; 63:687-695
3. Delgado-Aros S, Kim D-Y, Burton D, et al. Effect of GLP-1 on gastric volume, emptying, maximum volume ingested, and postprandial symptoms in humans. American journal of physiology Gastrointestinal and liver physiology 2002; 282:31
4. van Can J, Sloth B, Jensen C B, et al. Effects of the once-daily GLP-1 analog liraglutide on gastric emptying, glycemic parameters, appetite and energy metabolism in obese, non-diabetic adults. International journal of obesity 2014; 38:784-793
5. Peters A. Incretin-based therapies: review of current clinical trial data. The American journal of medicine 2010; 123:S28-37
6. Verdich C, Flint A, Gutzwiller J P, et al. A meta-analysis of the effect of glucagon-like peptide-1 (7-36) amide on ad libitum energy intake in humans. The Journal of Clinical Endocrinology & Metabolism 2001; 86:4382-4389
7. Bray G, Ryan D. Update on obesity pharmacotherapy. Annals of the New York Academy of Sciences 2014
8. Linnebjerg H, Park S, Kothare P A, et al. Effect of exenatide on gastric emptying and relationship to postprandial glycemia in type 2 diabetes. Regulatory peptides 2008; 151:123-129
9. Moreno J, Willett K, Desilets A. Exenatide as a novel weight loss modality in patients without diabetes. Ann Pharmacother 2012; 46:1700-1706
10. Batterham R L, Cowley M A, Small C J, et al. Gut hormone PYY(3-36) physiologically inhibits food intake. Nature 2002; 418:650-654
11. Flegal K M, Carroll M D, Kit B K, Ogden C L. Prevalence of obesity and trends in the distribution of body mass index among US adults, 1999-2010. JAMA: the journal of the American Medical Association 2012; 307:491-497
12. Gardiner J V, Jayasena C N, Bloom S R. Gut hormones: a weight off your mind. J Neuroendocrinol 2008; 20:834-841
13. Jayasena C N, Bloom S R. Role of Gut Hormones in Obesity. Endocrinology & Metabolism Clinics of North America 2008; 37:769-787
14. Koda S, Date Y, Murakami N, et al. The role of the vagal nerve in peripheral PYY(3-36)-induced feeding reduction in rats. Endocrinology 2005; 146:2369-2375
15. le Roux C W, Batterham R L, Aylwin S J, et al. Attenuated peptide YY release in obese subjects is associated with reduced satiety. Endocrinology 2006; 147:3-8
16. Lenard N R, Berthoud H-R. Central and Peripheral Regulation of Food Intake and Physical Activity: Pathways and Genes. Obesity 2008; 16:S11-S22
17. Ogden C L, Yanovski S Z, Carroll M D, Flegal K M. The epidemiology of obesity. Gastroenterology 2007; 132:2087-2102

What is claimed is:

1. A pharmaceutical composition comprising Peptide YY (PYY) in a dose of about 2.5 µg to about 250 µg, and a pharmaceutically acceptable excipient, wherein the composition provides satiation to a subject and minimizes or eliminates any substantial systemic delivery of PYY in the plasma of the subject, wherein the composition is formulated as an oral dissolving tablet, and wherein the pharmaceutically acceptable excipient is selected from the group consisting of stabilizers, preservatives, antioxidants, buffers, surfactants, rheology modifiers, and mucosal permeation enhancers.

2. The pharmaceutical composition of claim 1, wherein the PYY is PYY(3-36).

3. The pharmaceutical composition of claim 1, wherein the dose of PYY is about 2.5 µg.

4. The pharmaceutical composition of claim 1, wherein the dose of PYY is about 25 µg.

5. The pharmaceutical composition of claim 1, wherein the dose of PYY is about 250 µg.

6. The pharmaceutical composition of claim 2, wherein the pharmaceutically acceptable excipient comprises propylene glycol, potassium sorbate, I-arginine, edetate disodium, monosodium phosphate, and polysorbate 20.

7. The pharmaceutical composition of claim 2, wherein the dose of PYY(3-36) in the pharmaceutical composition is at least about 25 µg.

8. The pharmaceutical composition of claim 1, further comprising one or more active pharmaceutical ingredients selected from the group consisting of Glucagon-like peptide-1 (GLP-1), oxyntomodulin (OXM), and cholecystokinin acetyl-CoA carboxylase-(ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMP-activated protein kinase (AMPK) activator, a sulfonylurea, a meglitinide, an α-amylase inhibitor, an α-glucoside hydrolase inhibitor, an α-glucosidase inhibitor, a peroxisome proliferator-activated receptor gamma (PPARγ) agonist, a PPAR α/γ agonist, a biguanide, a GLP-1 modulator, a GLP-1 receptor agonist, a protein tyrosine phosphatase-IB (PTP-IB) inhibitor, a sirtuin-1 (SIRT-1) activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a vasoactive intestinal peptide receptor 2 (VPAC2) receptor agonist, a sodium glucose co-transporter 2 (SGLT2) inhibitor, a glucagon receptor modulator, a G protein-coupled receptor 19 (GPCR19) modulator, a fibroblast growth factor 21 (FGF21) derivative or analog, a free fatty acid receptor 1 (FFA1) agonist, a free fatty acid receptor 4 (FFA4) modulators, a high affinity nicotinic acid receptor (HM74A) activator, a sodium-D-glucose cotransporter (SGLTI) inhibitor, an inhibitor or modulator of a carnitine palmitoyl transferase enzyme, a fructose 1,6-diphosphatase inhibitor, an aldose reductase inhibitor, a mineralocorticoid receptor inhibitor, a target of rapamycin kinase multiprotein complex (TORC2) inhibitor, a C-C chemokine receptor type 2 (CCR2) and/or a C-C chemokine receptor type 5 (CCR5) inhibitor, a protein kinase C (PKC) inhibitor, a fatty acid synthetase inhibitor, a serine palmitoyl transferase inhibitor, a G protein-coupled receptor 81 (GPR81) modulator, a G protein-coupled receptor 39 (GPR39) modulator, a G protein-coupled receptor 43 (GPR43) modulator, a G protein-coupled receptor 41 (GPR41) modulator, a G protein-coupled receptor 105 (GPR105) modulator, voltage-gated potassium channel (Kv1.3), retinal binding protein 4, glucocorticoid receptor, a somatostatin receptor, an inhibitor or modulator of pyruvate dehydrogenase kinase isoform 2 (PDHK2) or pyruvate dehydrogenase kinase isoform 4 (PDHK4), an inhibitor of mitogen-activated protein kinase kinase kinase kinase 4 (MAP4K4), an interleukin 1 modulator, a 3-hydroxy-3-methyl-glutaryl-coenzyme A (HMG-CoA) reductase inhibitor, a squalene synthetase inhibitor, a fibrate, a bile acid sequestrant, an acyl-CoA cholesterol acyltransferase (ACAT) inhibitor, a microsomal triglyceride transfer protein (MTP) inhibitor, a lipooxygenase inhibitor, a cholesterol absorption inhibitor, a proprotein convertase subtilisin/kexin type 9 (PCSK9) modulator, a cholesteryl ester transfer protein inhibitor, a modulator of retinoid x receptor α (RXRα), a gastric inhibitory polypeptide receptor (GIP) agonist, enterostatin or an enterostatin analog, amylin or an amylin receptor agonist, a ghrelin modulator, leptin or a leptin receptor agonist, a pancreatic polypeptide (PP), calcitonin, neuropeptide Y (NPY), human growth hormone, prolactin, oxytocin, bovine growth hormone, porcine growth hormone, ghrelin, or glucagon.

9. The pharmaceutical composition of claim 1, wherein the preservative comprises sodium methyl paraben or sodium propyl paraben.

10. The pharmaceutical composition of claim 1, wherein the stabilizer comprises mannitol or sucrose.

11. The pharmaceutical composition of claim 1, wherein the mucosal permeation enhancer comprises gelatin.

12. The pharmaceutical composition of claim 1, wherein the pharmaceutically acceptable excipient further comprises a flavoring or sweetening agent.

13. The pharmaceutical composition of claim 12, wherein the sweetening agent comprises sorbitol, sucrose, or aspartame.

* * * * *

SEQUENCE LISTING

```
<160> NUMBER OF SEQ ID NOS: 2

<210> SEQ ID NO 1
<211> LENGTH: 34
<212> TYPE: PRT
<213> ORGANISM: Homo sapiens

<400> SEQUENCE: 1

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

```
<210> SEQ ID NO 2
<211> LENGTH: 1069
<212> TYPE: DNA
<213> ORGANISM: Homo sapiens

<400> SEQUENCE: 2
gcccctggag gaactgaacc cactatcggt catggggccg agactaaatg tggcgggttg      60
tctttaatct gctgccaaga ggaaactcat tcaggcaagt tcagcccttt atgaggaatt     120 ccctgtggt cacattccaa ttcctggacc tgctgccacc ctcagaactg catgctcctt     180
cttcagactt tctaagaatg actcaggtca ttggtggagt gaagtcaaga tttccaactc     240
agtcacctga agagatggag ataccattca tggagctgga ggtccctgga gatttgggaa     300
ttcagataac aagctaagat aaggagtttg cctacctctg tcctagagcg aagcctgagc     360
cttgggcgcg cagcacacca caagtatctg ttactgtgtt ttgcagaagc ttcaggcggg     420
gatataagcc ccacaaggaa agcgctgagc agaggaggcc tcagcttgac ctgcggcagt     480 gcagccttg ggacttccct cgccttccac ctcctgctcg tctgcttcac aagctatcgc     540
tatggtgttc gtgcgcaggc cgtggcccgc cttgaccaca gtgcttctgg ccctgctcgt     600
ctgcctaggg gcgctggtcg acgcctaccc catcaaaccc gaggctcccg gcgaagacgc     660
ctcgccggag gagctgaacc gctactacgc ctccctgcgc cactacctca acctggtcac     720
ccggcagcgg tatgggaaaa gagacggccc ggacacgctt cttttccaaaa cgttcttccc     780 cgacggcgag gaccgccccg tcaggtcgcg gtcggagggc ccagacctgt ggtgaggacc     840
cctgaggcct cctgggagat ctgccaacca cgcccacgtc atttgcatac gcactcccga     900
ccccagaaac ccggattctg cctcccgacg gcggcgtctg ggcagggttc gggtgcggcc     960
ctccgcccgc gtctcggtgc ccccgccccc tgggctggag ggctgtgtgt ggtccttccc    1020
tggtcccaaa ataaagagca aattccacag aaacggaaaa aaaaaaaa                  1069
```